(12) United States Patent
Towe

(10) Patent No.: US 11,497,907 B2
(45) Date of Patent: Nov. 15, 2022

(54) DIPOLAR ANTENNA SYSTEM AND RELATED METHODS

(71) Applicant: Arizona Board of Regents on behalf of Arizona State University, Scottsdale, AZ (US)

(72) Inventor: Bruce C. Towe, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 105 days.

(21) Appl. No.: 16/673,745

(22) Filed: Nov. 4, 2019

(65) Prior Publication Data

US 2020/0061368 A1 Feb. 27, 2020

Related U.S. Application Data

(63) Continuation of application No. 15/621,208, filed on Jun. 13, 2017, now Pat. No. 10,463,856, which is a continuation of application No. 13/735,716, filed on Jan. 7, 2013, now Pat. No. 9,700,712, which is a continuation-in-part of application No.
(Continued)

(51) Int. Cl.
| | |
|---|---|
| *A61N 1/05* | (2006.01) |
| *H01P 11/00* | (2006.01) |
| *A61N 1/36* | (2006.01) |
| *A61N 1/372* | (2006.01) |
| *A61N 1/378* | (2006.01) |
| *H01Q 9/00* | (2006.01) |

(52) U.S. Cl.
CPC ............. *A61N 1/05* (2013.01); *A61N 1/3605* (2013.01); *A61N 1/3787* (2013.01); *A61N 1/37205* (2013.01); *A61N 1/37223* (2013.01); *H01P 11/00* (2013.01); *H01Q 9/00* (2013.01); *Y10T 29/49018* (2015.01)

(58) Field of Classification Search
CPC .... A61N 1/05; A61N 1/3605; A61N 1/37205; A61N 1/37223; A61N 1/3787; H01P 11/00; H01Q 9/00; Y10T 29/49018
USPC .......................................................... 607/62
See application file for complete search history.

(56) References Cited

U.S. PATENT DOCUMENTS

| | | |
|---|---|---|
| 4,057,069 A | 11/1977 | Dorffer et al. |
| 4,289,134 A | 9/1981 | Bernstein |

(Continued)

FOREIGN PATENT DOCUMENTS

| | | |
|---|---|---|
| KR | 200391529 | 8/2005 |
| WO | 1999006108 | 2/1999 |

(Continued)

OTHER PUBLICATIONS

International Search Report and Written Opinion for PCT Application No. PCT/US2010/035753, 11 pages. Jan. 18, 2011. Jan. 18, 2011.

(Continued)

*Primary Examiner* — Erin M Piateski
(74) *Attorney, Agent, or Firm* — Bryan Cave Leighton Paisner LLP

(57) ABSTRACT

Some embodiments include a dipolar antenna system to electrically power an implantable miniature device and/or to stimulate bioelectrically excitable tissue. Other related systems and methods are also disclosed.

18 Claims, 17 Drawing Sheets

Related U.S. Application Data

PCT/US2011/049966, filed on Aug. 31, 2011, and a continuation-in-part of application No. 13/321,770, filed as application No. PCT/US2010/035753 on May 21, 2010, now Pat. No. 8,909,343, said application No. 13/735,716 is a continuation-in-part of application No. 13/703,288, filed as application No. PCT/US2011/039642 on Jun. 8, 2011, now Pat. No. 8,725,270.

(60) Provisional application No. 61/583,930, filed on Jan. 6, 2012, provisional application No. 61/583,953, filed on Jan. 6, 2012, provisional application No. 61/378,716, filed on Aug. 31, 2010, provisional application No. 61/180,549, filed on May 22, 2009, provisional application No. 61/352,639, filed on Jun. 8, 2010.

(56) References Cited

U.S. PATENT DOCUMENTS

| | | | |
|---|---|---|---|
| 4,679,572 | A | 7/1987 | Baker, Jr. |
| 4,901,084 | A | 2/1990 | Huguenin et al. |
| 4,935,345 | A | 6/1990 | Guilbeau et al. |
| 5,466,348 | A | 11/1995 | Holm-Kennedy |
| 6,647,296 | B2 | 11/2003 | Fischell et al. |
| 6,668,197 | B1 | 12/2003 | Habib et al. |
| 7,024,248 | B2 | 4/2006 | Penner et al. |
| 7,174,037 | B2 | 2/2007 | Arnone et al. |
| 7,702,395 | B2 | 4/2010 | Towe et al. |
| 8,282,561 | B2 | 10/2012 | Towe |
| 8,340,773 | B2 | 12/2012 | Towe et al. |
| 8,369,956 | B2 | 2/2013 | Towe et al. |
| 8,626,303 | B2 | 1/2014 | Towe et al. |
| 8,725,270 | B2 | 5/2014 | Towe |
| 8,774,928 | B2 | 7/2014 | Towe et al. |
| 8,909,343 | B2 | 12/2014 | Towe |
| 9,446,255 | B2 | 9/2016 | Towe et al. |
| 9,457,196 | B2 | 10/2016 | Towe et al. |
| 9,555,258 | B2 | 1/2017 | Towe et al. |
| 9,693,708 | B2 | 7/2017 | Towe |
| 10,016,612 | B2 | 7/2018 | Towe et al. |
| 10,022,566 | B2 | 7/2018 | Towe |
| 10,252,085 | B2 | 4/2019 | Towe et al. |
| 10,441,803 | B2 | 10/2019 | Towe et al. |
| 2002/0169354 | A1 | 11/2002 | Munro, III |
| 2006/0079936 | A1 | 4/2006 | Boveja et al. |
| 2006/0161225 | A1 | 7/2006 | Sormann et al. |
| 2006/0167500 | A1 | 7/2006 | Towe et al. |
| 2007/0006653 | A1 | 1/2007 | Kim |
| 2007/0185551 | A1 | 8/2007 | Meadows et al. |
| 2007/0293910 | A1 | 12/2007 | Strother et al. |
| 2008/0108915 | A1 | 5/2008 | Penner |
| 2008/0188909 | A1 | 8/2008 | Bradley |
| 2008/0208293 | A1 | 8/2008 | Parramon et al. |
| 2008/0215112 | A1 | 9/2008 | Firlik et al. |
| 2008/0306359 | A1* | 12/2008 | Zdeblick ............ A61N 1/37217 600/302 |
| 2009/0204170 | A1 | 8/2009 | Hastings et al. |
| 2011/0023289 | A1* | 2/2011 | Finn ................ G06K 19/07745 29/601 |
| 2011/0118721 | A1 | 5/2011 | Brannan |
| 2012/0041310 | A1 | 2/2012 | Towe |
| 2012/0248888 | A1* | 10/2012 | Kesler ..................... H03H 7/40 307/104 |
| 2013/0096435 | A1 | 4/2013 | Towe |
| 2014/0172047 | A1 | 6/2014 | Spitaels et al. |
| 2015/0148710 | A1 | 5/2015 | Towe et al. |
| 2015/0306429 | A1 | 10/2015 | Towe et al. |
| 2017/0056676 | A1 | 3/2017 | Towe et al. |
| 2017/0258363 | A1 | 9/2017 | Towe |
| 2018/0093112 | A1 | 4/2018 | Towe et al. |
| 2019/0247668 | A1 | 8/2019 | Towe et al. |
| 2019/0282835 | A1 | 9/2019 | Towe et al. |
| 2019/0336777 | A1 | 11/2019 | Towe et al. |

FOREIGN PATENT DOCUMENTS

| | | | |
|---|---|---|---|
| WO | 2003107372 | 12/2003 | |
| WO | 2004016315 | 2/2004 | |
| WO | 2004069129 | 8/2004 | |
| WO | 2004105583 | 12/2004 | |
| WO | 2005120203 | 12/2005 | |
| WO | 2008137703 | 11/2008 | |
| WO | 2010027963 | 3/2010 | |
| WO | 2010135634 | 11/2010 | |
| WO | WO-2010135634 A2 * | 11/2010 | ............... A61N 1/06 |
| WO | 2011156495 | 12/2011 | |
| WO | 2012030962 | 3/2012 | |
| WO | 2013071290 | 5/2013 | |
| WO | 2013169363 | 11/2013 | |
| WO | 2013176744 | 11/2013 | |
| WO | 2014093332 | 6/2014 | |
| WO | 2015069446 | 5/2015 | |
| WO | 2015142842 | 9/2015 | |

OTHER PUBLICATIONS

Glenn, W.W.L., et al., "Electrical Stimulation of Excitable Tissue by Radio-Frequency Transmission," Annals of Surgery, Sep. 1954, pp. 338-350, vol. 150, No. 3. Sep. 1954.

Miatthaei, G.L., et al., "A Study of the Optimum Design of Wide-Band Parametric Amplifiers and Up-Converters," IRE Transactions on Microwave Theory and Techniques, Jan. 1961, pp. 23-28, vol. MTT-10. Jan. 1961.

Sard, E., et al., "A Positive Resistance Up-Converter for Ultra-Low-Noise Amplification," IEEE Transactions on Microwave Theory and Techniques, Dec. 1966, pp. 608-618, vol. MTT-14, No. 12. Dec. 1966.

Towe, B.C., "Passive Biotelemetry by Frequency Keying," IEEE Transactions on Biomedical Engineering, Oct. 1986, pp. 905-909, vol. BME-33, No. 10. Oct. 1986.

Heetderks, W, "RF Powering of Millimeter- and Submillimeter-Sized Neural Prosthetic Implants," IEEE Transactions on Antennas and Propagation, May 1988, p. 323, vol. 35, No. 5. May 1988.

Wise, K.D., et al., "Wireless Implantable Microsystems: High-Density Electronic Interfaces to the Nervous System," Proceedings of the IEEE, Jan. 2004, pp. 76-97, vol. 92, No. 1. Jan. 2004.

Poon, A.S.Y., et al., "Optimal Frequency for Wireless Power Transmission into Dispersive Tissue," IEEE Transactions on Antennas and Propagation, May 2010, pp. 1739-1749, vol. 58, No. 5. May 2010.

Moheseni et al., "Wireless Multichannel Biopotential Recording Using an Integrated Fm Telemetry Circuit," Sep. 2005.

Dehennis et al., A Double-Sided Single-Chip Wireless Pressure Sensor, Micro Electro Meeh. Sys., 15th IEEE Intl. Conf., 252-255, 2002. 2002.

Harpster et al., "A passive wireless integrated humidity sensor", Sensors Actuators A: Physical, 95(2-3): 100-07, 2002. 2002.

Lindsey et al., "A new technique for transmission of signals from implantable tranducers," IEEE Trans. Biomed. Engineering, 45(5):614-619, 1998. 1998.

Sun et al., "Data communication between brain implants and computer," IEEE Trans. Neural Sys. Rehab. Engin., 11 (2): 189-192, 2003. 2003.

Takahata et al., In: Stentenna: A Micromachined Antenna Stent for Wireless Monitoring of Implantable Microsensors, Eng. Med. Biol. Soc., Proc. 25th Ann. Intl. Conf. IEEE, 4:3360-3363, 2003. 2003.

Towe, "Passive Backscatter Biotelemetry for Neural Interfacing," Proceedings of the 3rd International IEEE EMBS Conference on Neural Engineering, Kohala Coast, Hawaii, p. 144-147, May 2-5, 2007 May 2, 2007.

International Preliminary Report on Patentability for PCT Application No. PCT/US2010/035753, 6 pages, dated Nov. 22, 2011. Nov. 22, 2011.

(56) References Cited

OTHER PUBLICATIONS

International Search Report and Written Opinion for PCT Application No. PCT/US2011/039642, 7 pages, dated Feb. 17, 2012. Feb. 17, 2012.
International Preliminary Report on Patentability for PCT Application No. PCT/US2011/039642, 5 pages, dated Dec. 10, 2012. Dec. 10, 2012.
International Preliminary Report on Patentability of International Patent Application No. PCT/US09/55594, 6 pages, dated Mar. 8, 2011. Mar. 8, 2011.
International Search Report and Written Opinion for International Patent Application No. PCT/US09/55594, 8 pages, dated Nov. 13, 2009. Nov. 13, 2009.

\* cited by examiner

- 1905 — Providing a dipolar antenna configured to receive a dipolar electric field, the dipolar antenna comprising a first conductive element and a second conductive element
- 1910 — Providing a rectifier
- 1915 — Providing a resistor
- 1920 — Providing a voltage limiter
- 1925 — Providing a capacitor
- 1930 — Coupling the rectifier electrically in parallel with the resistor and the voltage limiter to form a sub-circuit
- 1935 — Coupling the sub-circuit electrically in series with the first conductive element, the capacitor, and the second conductive element to form an apparatus configured to be implanted in biological tissue
- 1940 — Coupling electrically a first rectifier connector of the rectifier, a first resistor connector of the resistor, and a first voltage limiter connector of the voltage limiter with a first element connector of the first electrically conductive element
- 1945 — Coupling electrically a second rectifier connector of the rectifier, a second resistor connector of the resistor, and a second voltage limiter connector of the voltage limiter with a first capacitor connector of the capacitor
- 1950 — Coupling electrically a second capacitor connector of the capacitor with a second element connector of the second electrically conductive element
- 1955 — Providing an electromagnetic wave exciter configured to emit electromagnetic radiation comprising the dipolar electric field
- 1960 — Coupling electrically the first electrically conductive element and the second electrically conductive element with the biological tissue

DIPOLAR ANTENNA SYSTEM AND RELATED METHODS

CROSS-REFERENCE TO RELATED APPLICATIONS

This application is a continuation of U.S. Non-Provisional application Ser. No. 15/621,208, filed Jun. 13, 2017. U.S. Non-Provisional application Ser. No. 15/621,208 is a continuation of U.S. Non-Provisional patent application Ser. No. 13/735,716, filed Jan. 7, 2013, which claims the benefit of U.S. Provisional Patent Application No. 61/583,930, filed Jan. 6, 2012, and U.S. Provisional Patent Application No. 61/583,953, filed Jan. 6, 2012.

Further, U.S. Non-Provisional application Ser. No. 13/735,716 is a continuation-in-part of International Patent Application Serial No. PCT/US2011/049966, filed Aug. 31, 2011, U.S. patent application Ser. No. 13/321,770, filed Apr. 5, 2012, and U.S. patent application Ser. No. 13/703,288, filed Dec. 10, 2012. International Patent Application Serial No. PCT/US2011/049966 claims the benefit of U.S. Provisional Patent Application No. 61/378,716, filed Aug. 31, 2010. Meanwhile, U.S. patent application Ser. No. 13/321,770 is a national stage application based on International Patent Application Serial No. PCT/US2010/035753, filed May 21, 2010, which claims the benefit of U.S. Provisional Patent Application Ser. No. 61/180,549, filed May 22, 2009; and U.S. patent application Ser. No. 13/703,288 is a national stage application based on International Patent Application Serial No. PCT/US2011/039642, filed Jun. 8, 2011, which claims the benefit of U.S. Provisional Patent Application No. 61/352,639, filed Jun. 8, 2010.

U.S. Non-Provisional application Ser. No. 15/621,208, U.S. Non-Provisional application Ser. No. 13/735,716, International Patent Application Serial No. PCT/US2011/049966, U.S. patent application Ser. No. 13/321,770, U.S. patent application Ser. No. 13/703,288, International Patent Application Serial No. PCT/US2010/035753, International Patent Application Serial No. PCT/US2011/039642, U.S. Provisional Patent Application No. 61/378,716, U.S. Provisional Patent Application Ser. No. 61/180,549, U.S. Provisional Patent Application No. 61/352,639, U.S. Provisional Patent Application No. 61/583,930, and U.S. Provisional Patent Application No. 61/583,953 are incorporated herein by reference in their entirety.

STATEMENT REGARDING FEDERALLY SPONSORED RESEARCH OR DEVELOPMENT

This invention was made with government support under NS059815 awarded by the National Institutes of Health. The government has certain rights in the invention.

FIELD OF THE INVENTION

This invention relates generally to dipolar antennas, and relates more particularly to dipolar antennas for electrically powering bioelectronic medical implants and/or for stimulating bioelectrically excitable tissues, and related methods of implantation, manufacture, and/or use.

DESCRIPTION OF THE BACKGROUND

Bioelectronic medical implants (e.g., stimulators, sensors, communication systems, actuators, etc.) can be useful for monitoring and controlling physiologic function. Making bioelectronic medical implants as small as possible can reduce the invasiveness of such implants and thereby mitigate or eliminate trauma and complications brought about by introducing such implants into a body. Further, non-surgically introducing these implants into the body can reduce the expense of use and make available more applications of use of these implants, permitting increased use of these implants in biomedicine.

Bioelectronic medical implants generally rely on an energy source to electrically power the implants. Typical energy sources can include an implanted battery and/or an external energy transfer system that induces energy into the body. In the latter example, energy can be induced for direct use by the implant and/or to charge an implanted battery. Many existing external energy transfer systems for bioelectronic medical implants use coaxially coupled magnetic induction coils—one internal to a body and one external to the body—forming a transformer. These induction coils are conventionally magnetically coupled because the transparency of the magnetic field can mitigate energy dissipation in the body tissue, resulting in a tolerable generation of heat in the body tissue. For example, a conventional external exciter can include an electrically powered box having a 1-4 centimeter diameter loop inductive coil configured to be electrically powered at radio frequencies in the megahertz region. Meanwhile, a corresponding internal bioelectronic medical implant can have a corresponding loop inductive coil. Accordingly, under the coaxial approach, a magnetic coupling between the coils can induce energy from the external exciter to the internal implant.

The size of the coils can affect and/or define the efficiency with which energy is transferred between the coils. For example, the coupling coefficient of the two coils can depend on the diameters of the coils and the depth of the internal coil in the body. Specifically, because coupling coefficients can decline rapidly, in some cases by the cube of the separation distance of the coils, implanting the internal coil in a body no farther than a distance equivalent to half the diameters of the coils can provide a desirable coupling coefficient of the two coils.

Further, the efficiency of magnetically coupled external energy transfer systems can depend on having two inductor coils coupled by magnetic field lines threading the open areas of the coils. Because the induced electrical energy of the inductor coils is proportional to the loop areas of the inductor coils, using a form factor that has significant length and open width in order to enclose a magnetic path can increase the efficiency of the inductive coupling there between. Thus, it follows that a bioelectronic medical implant using radio frequency magnetic induction can be constrained and/or designed in size and dimension to be equal to the implant inductor loop antenna outer dimension. This in turn can define a size of a surgical opening for implanting a bioelectronic medical implant in a patient's body. Clearly, small entrance wounds are less invasive and/or harmful to the patient's body, yet as mentioned previously, small area inductor loops can be inefficient and present problems of low coupling coefficients that limit functional energy transfer to bioelectronic medical implants when they are placed at depth. Similarly, microwave slot antennas and radiator open lumen loops are coupled primarily to the incident magnetic field.

In addition to electrically powering bioelectronic medical implants, external energy transfer systems can also be used to stimulate bioelectrically excitable tissue. Stimulating bioelectrically excitable tissue can allow the function of the tissue to be manipulated or modified, thus providing a therapeutic or otherwise desirable biological effect. For example, neurostimulation may be used for restoring bodily function in cases of neural injury or disease. Neurostimulation in this context refers to the stimulation of electrically excitable tissues of living things. This can include, for example, the human tissues of the brain, muscle, and/or nervous system.

In practice, electrical currents applied to tissue can affect the membranes of excitable cells of the tissue, causing a depolarizing effect that can lead to a cell action event that depends on its type and biological function. Meanwhile, pulsing electrical currents can fulfill certain physiologic conditions that enable the electricity to be effective.

Applying electrical currents to the body surface can cause the electrical currents to diffuse in the volume conductivity of tissue and attenuate according to well known laws. These electrical currents can also stimulate near-surface nerves and muscle tissues to some degree, but may not be able to reach deeper tissues because of high electrical losses in tissue. Attempting to compensate for these electrical losses may result in raising the current levels high enough to cause electrical shock.

Stimulating bioelectronically excitable tissue can be achieved by applying pulsed electrical currents directly to tissue via surface electrodes at the tissue surface and/or implanted electrodes within the tissue. However, the strong diffusion of electrical current in tissue from surface electrodes means that specific stimulation of a given nerve or nerve fiber within a bundle is very difficult and rather there is a tendency for electrical currents applied to the body surface to broadly stimulate in undesirable ways. Implantable electrodes can overcome these problems, yet like with conventional systems for electrically powering bioelectronic medical implants, are typically invasive and conventionally are supplied energy by wires running through the skin and/or bulky implanted energy sources, such as, for example, a battery and/or an inductor coil of an external radio frequency energy transfer system.

For example, like for conventional systems for electrically powering bioelectronic medical devices, electrical currents can be delivered to tissues by way of radio frequency induction to a bioelectronic medical implant. These systems typically use an inductor implanted within the body to magnetically couple to an external radio frequency field. However, these implants are generally relatively large and can be on the order of a centimeter in size.

Despite the use of magnetically coupled external energy transfer systems, capacitively coupled (i.e., electric field coupled) external energy transfer systems have largely been ignored and have been considered ineffective for powering bioelectronic medical implants and/or stimulating bioelectrically excitable tissue.

Meanwhile, having identified numerous drawbacks associated with magnetically coupled external energy transfer systems, a need or potential for benefit exists for a system for electrically powering a bioelectronic medical device and/or for stimulating bioelectrically excitable tissue that allows for non-invasive implantation, at depths in the biological tissue that are large relative to the implant cross-sectional area, without sacrificing functional energy transfer to the implanted device to a point that a desired level of stimulation cannot be met.

BRIEF DESCRIPTION OF THE DRAWINGS

To facilitate further description of the embodiments, the following drawings are provided in which:

FIG. 19 illustrates a flow chart for an embodiment of another method; and

Figure 1:
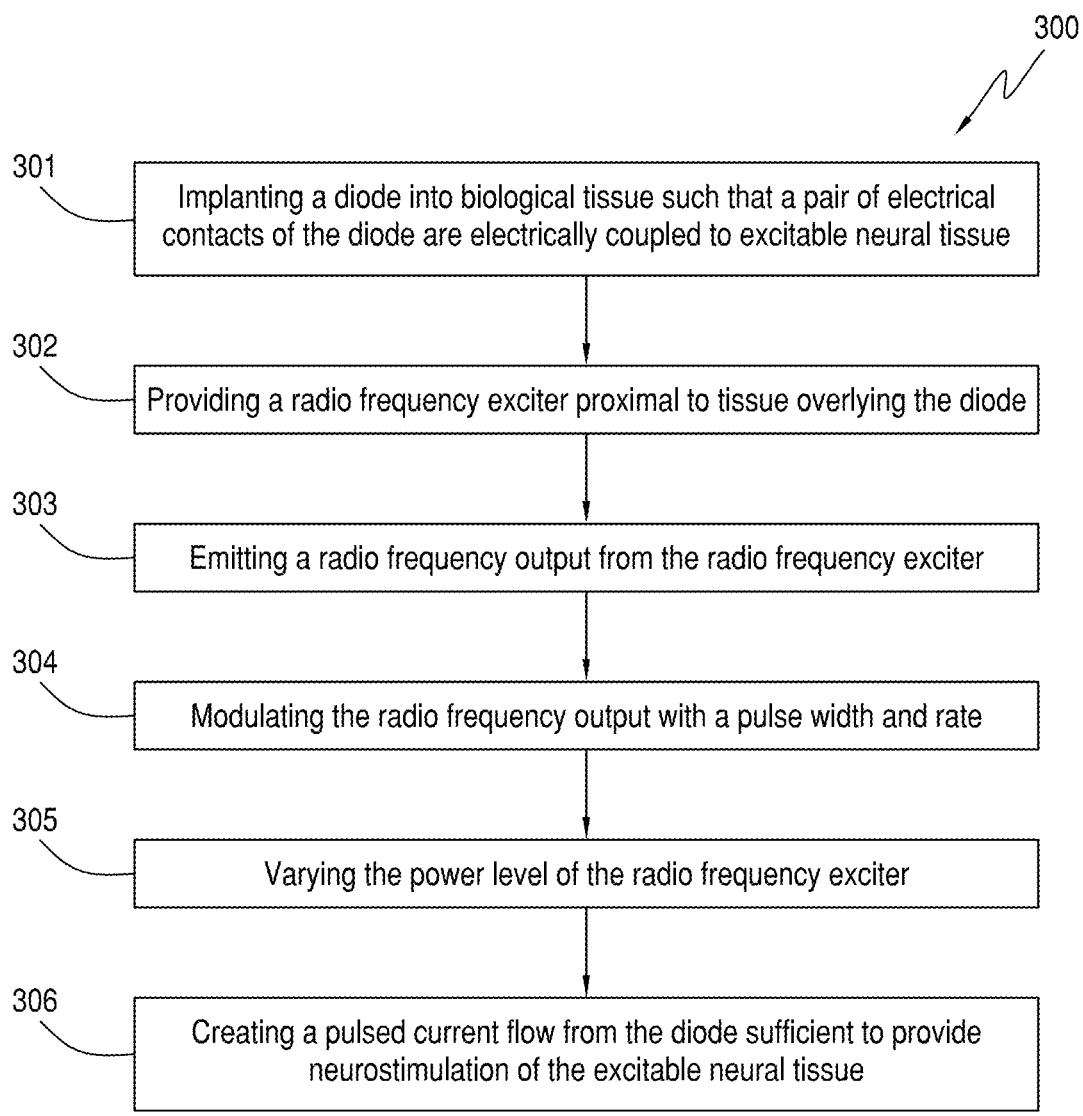
FIG. 1 is schematic flowchart diagram illustrating one embodiment of a method for providing neurostimulation.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments an apparatus. The apparatus can comprise a dipolar antenna comprising (i) a first electrically conductive element having a first length and a first width, and (ii) a second electrically conductive element having a second length and a second width. The dipolar antenna can be configured to be implanted in biological tissue and/or to receive a dipolar electric field. Meanwhile, a combined length of the first length and the second length can be greater than or equal to approximately 2 millimeters and less than or equal to approximately 6 centimeters, and the first width and the second width each can be less than or equal to approximately 1.5 millimeters.

In these embodiments, the apparatus can comprise an electromagnetic wave exciter configured to emit electromagnetic radiation comprising the dipolar electric field. The apparatus can be configured to transfer energy between the electromagnetic wave exciter and the dipolar antenna through the dipolar electric field of the electromagnetic radiation.

Further, the electromagnetic radiation can have a frequency between approximately 300 Megahertz and approximately 30 Gigahertz. For example, the electromagnetic radiation can have a frequency of approximately 915 Megahertz or approximately 2.45 Gigahertz.

Also, in these embodiments, the apparatus can comprise an electronic device and/or an energy storage device electrically coupled to the electronic device. The dipolar antenna can be configured to provide energy to the electronic device and/or the energy storage device.

Further, the electronic device can comprise a bioelectronic medical sensor, a transducer, a communication system, and/or an actuator. Likewise, the energy storage device can comprise a battery. Also. the electronic device can further comprise a rectifier, and the rectifier can comprise a diode and/or a microcontroller.

Also, in these embodiments, the apparatus can comprise a syringe. The dipolar antenna can be located within the syringe.

Some embodiments include a method of implanting a first electronic device into biological tissue. The method can comprise inserting a needle of a syringe into the biological tissue. The syringe can contain the first electronic device. Meanwhile, the first electronic device can comprise a dipolar antenna, and the dipolar antenna can comprise a first electrically conductive element having a first end and a second electrically conductive element having a second end. Further, the first electronic device can comprise a second electronic device and/or an energy storage device electrically coupled to the second electronic device. The first end and the second end can be electrically coupled to the second electronic device and/or the energy storage device electrically coupled to the second electronic device to permit the dipolar antenna to provide a current to the second electronic device. The method can further comprise ejecting the first electronic device from the syringe into the biological tissue, and removing the needle of the syringe from the biological tissue such that the first electronic device remains disposed within the biological tissue.

Meanwhile, some embodiments include a method. The method can comprise: providing a dipolar antenna in a biological tissue, wherein the dipolar antenna comprises a first electrically conductive element comprising a first end that is electrically coupled to a second end of a second electrically conductive element; transmitting a dipolar electric field to the dipolar antenna while the dipolar antenna is in the biological tissue; inducing a current flow in the dipolar antenna while the dipolar antenna is in the biological tissue; and providing the current flow to a load of an electronic device and/or an energy storage device electrically coupled to the electronic device while the dipolar antenna is in the biological tissue.

In these embodiments, transmitting the dipolar electric field to the dipolar antenna can comprise emitting electromagnetic radiation from an electromagnetic wave exciter. Emitting the electromagnetic radiation from the electromagnetic wave exciter can comprise: positioning the electromagnetic wave exciter proximate to an outer surface of the biological tissue; modulating the electromagnetic radiation from the electromagnetic wave exciter at a frequency of greater than or equal to approximately 300 Megahertz and less than or equal to approximately 30 Gigahertz, such as, for example, modulating the electromagnetic radiation from the electromagnetic wave exciter at a frequency of approximately 915 Megahertz or approximately 2.45 Gigahertz; and/or pulsing the electromagnetic radiation for a time period of greater than or equal to approximately 1 microsecond and less than or equal to approximately 10 milliseconds, at a frequency of greater than or equal to approximately 0.5 pulses per second and less than or equal to approximately 2,000 pulses per second.

Some embodiments include a method of manufacturing an energy supply for an electronic device. The method can comprise: coupling a first electrically conductive element to an electronic device; and coupling a second electrically conductive element to the electronic device. The first and second electrically conductive elements can form a dipolar antenna, the first electrically conductive element can have a first length and a first width, and the second electrically conductive element can have a second length and a second width.

In these embodiments, the electromagnetic wave exciter can be configured to emit the electromagnetic radiation at a frequency between approximately 300 Megahertz and approximately 30 Gigahertz, such as, for example, approximately 915 Megahertz. or approximately 2.45 Gigahertz. Further, the electromagnetic wave exciter can comprise an energy source capable of supplying a peak power level greater than or equal to approximately 50 watts and less than or equal to approximately 100 watts and an average power level greater than or equal to approximately 1 watt and less than or equal to approximately 10 watts. Further still, the electromagnetic wave exciter can be configured to pulse the electromagnetic radiation for a time period of greater than or equal to approximately 1 microsecond and less than or equal to approximately 10 milliseconds, at a frequency of greater than or equal to approximately 0.5 pulses per second and less than or equal to approximately 2,000 pulses per second.

Also, in these embodiments, the electromagnetic wave exciter can comprise an additional dipolar antenna. Further, the first electrically conductive element and/or the second electrically conductive element can comprise a biocompatible material (e.g., platinum, tungsten, palladium, and/or gold) and/or an insulating outer layer comprising a biocompatible polymer. Further still, the dipolar antenna can be configured to pass through a lumen of a 14 gauge needle, a 15 gauge needle, a 16 gauge needle, a 17 gauge needle, an 18 gauge needle, a 19 gauge needle, a 20 gauge needle, a 21 gauge needle, and/or a 22 gauge needle of a syringe.

Some embodiments include a system. The system comprises an apparatus. Further, the apparatus can comprise a dipolar antenna comprising a first electrically conductive element and a second electrically conductive element, a sub-circuit, and a capacitor. The apparatus can be configured to be implanted in biological tissue, and the dipolar antenna can be configured to receive a dipolar electric field. Further, the sub-circuit can comprise a rectifier, a resistor, and a voltage limiter. The rectifier, the resistor, and the voltage limiter can be electrically coupled in parallel with each other, and the first electrically conductive element, the sub-circuit, the capacitor, and the second electrically conductive element can be electrically coupled in series with each other.

In these embodiments, the system can also comprise an electromagnetic wave exciter configured to emit electromagnetic radiation comprising the dipolar electric field. Further, the system can be configured to transfer energy between the electromagnetic wave exciter and the dipolar antenna through the dipolar electric field of the electromagnetic radiation. The electromagnetic radiation can have a frequency greater than or equal to approximately 300 Megahertz and less than or equal to approximately 30 Gigahertz.

Also, in these embodiments, the first electrically conductive element can comprises a first element connector, the second electrically conductive element can comprise a second element connector, the rectifier can comprise a first rectifier connector and a second rectifier connector, the resistor can comprise a first resistor connector and a second resistor connector, the voltage limiter can comprise a first voltage limiter connector and a second voltage limiter connector, the capacitor can comprise a first capacitor connector and a second capacitor connector. The first rectifier connector, the first resistor connector, and the first voltage limiter connector can be electrically coupled to the first element connector, the second rectifier connector, the second resistor connector, and the second voltage limiter connector can be electrically coupled to the first capacitor connector, and the second capacitor connector can be electrically coupled to the second element connector. Meanwhile, the first electrically conductive element and the second electrically conductive element each can be configured to be electrically coupled with the biological tissue.

Also, in these embodiments, the biological tissue can comprise brain tissue, muscle tissue, and/or nervous system tissue. Further, the first electrically conductive element and/or the second electrically conductive element can comprise a biocompatible material (e.g., platinum, tungsten, palladium, and/or gold) and/or an insulating outer layer (e.g., a biocompatible polymer).

Also, in these embodiments, the system can comprise a syringe, and the apparatus can be located within the syringe.

Some embodiments include a method of providing a system. The method can comprise: providing a dipolar antenna configured to receive a dipolar electric field, the dipolar antenna comprising a first conductive element and a second conductive element; providing a rectifier; providing a resistor; providing a voltage limiter; providing a capacitor; coupling the rectifier electrically in parallel with the resistor and the voltage limiter to form a sub-circuit; and/or coupling the sub-circuit electrically in series with the first conductive element, the capacitor, and the second conductive element to form an apparatus configured to be implanted in biological tissue.

In these embodiments, the method can further comprise: electrically coupling a first rectifier connector of the rectifier, a first resistor connector of the resistor, and a first voltage limiter connector of the voltage limiter with a first element connector of the first electrically conductive element; electrically coupling a second rectifier connector of the rectifier, a second resistor connector of the resistor, and a second voltage limiter connector of the voltage limiter with a first capacitor connector of the capacitor; and electrically coupling a second capacitor connector of the capacitor with a second element connector of the second electrically conductive element.

Also, in these embodiments, the rectifier can comprise a Schottky diode. In some examples, the Schottky diode can comprise a Schottky diode system comprising one or more diodes, such as, for example, a bridge rectifier. Further, the voltage limiter can comprise a Zener diode; the resistor can comprise an electrical resistance greater than or equal to approximately 500 ohms and less than or equal to approximately 10,000 ohms, and/or the capacitor can comprise an electrical capacitance of greater than or equal to approximately 0.1 microfarads and less than or equal to 10 microfarads.

Some embodiments include a method. The method can comprise: inserting into biological tissue a needle of a syringe comprising an apparatus, the apparatus comprising: (a) a dipolar antenna comprising a first electrically conductive element and a second electrically conductive element, (b) a sub-circuit, and (c) a capacitor, wherein the dipolar antenna is configured to receive a dipolar electric field, the sub-circuit comprises a rectifier, a resistor, and a voltage limiter electrically coupled in parallel with each other, and the first electrically conductive element, the sub-circuit, the capacitor, and the second electrically conductive element are electrically coupled in series with each other; ejecting the apparatus from the syringe into the biological tissue via the needle; and removing the needle of the syringe from the biological tissue such that the apparatus remains disposed within the biological tissue.

In these embodiments, the method can further comprise, after inserting into the biological tissue the needle of the syringe comprising the apparatus, after ejecting the apparatus from the syringe into the biological tissue via the needle, and after removing the needle of the syringe from the biological tissue such that the apparatus remains disposed within the biological tissue, emitting electromagnetic radiation comprising the dipolar electric field towards the apparatus. Further, emitting electromagnetic radiation comprising the dipolar electric field towards the apparatus can comprise modulating the electromagnetic radiation at a frequency of greater than or equal to approximately 300 Megahertz and less than or equal to approximately 30 Gigahertz.

Also, in these embodiments, the method can further comprise, after inserting into the biological tissue the needle of the syringe comprising the apparatus, after ejecting the apparatus from the syringe into the biological tissue via the needle, and after removing the needle of the syringe from the biological tissue such that the apparatus remains disposed within the biological tissue, limiting an electrical voltage passing through the rectifier with the voltage limiter.

Referring initially to FIG. 1, an exemplary method 300 of providing neurostimulation to biological tissues is shown, according to an embodiment. This embodiment is not limiting. Other embodiments may comprise different combinations of the individual features shown and described in FIG. 1 or may comprise the features in a different order than that shown in FIG. 1.

Method 300 can comprise activity 301 of implanting a diode into biological tissue such that the electrical contacts of the diode are electrically coupled to excitable neural tissue. In this embodiment, method 300 also can comprise activity 302 of providing a radio frequency exciter proximal to tissue overlying the diode and activity 303 of emitting a radio frequency output from the radio frequency exciter. In specific embodiments, the output from the radio frequency exciter is an electric field in the microwave range. Method 300 also can comprise activity 304 of modulating the radio frequency output with a pulse width and rate and activity 305 of varying the power level of the radio frequency exciter. Furthermore, method 300 can comprise activity 306 of creating a pulsed current flow from the diode sufficient to provide neurostimulation of the excitable neural tissue.

Figure 2:
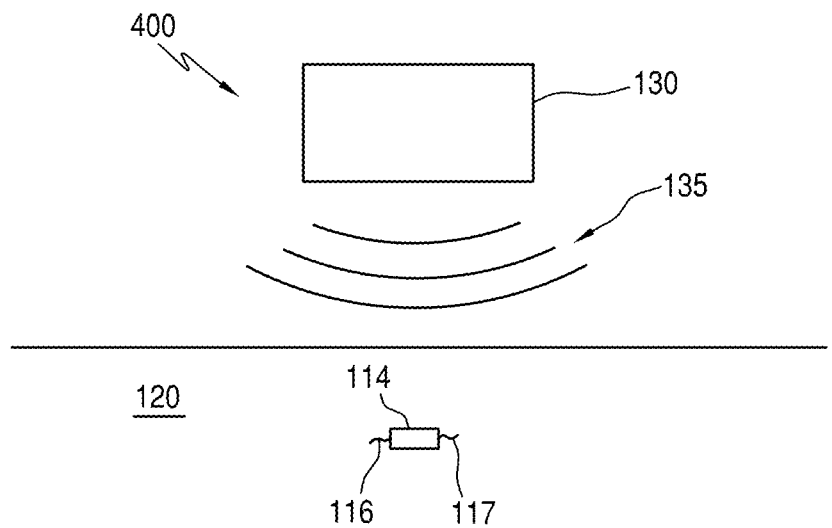
FIG. 2 is a schematic block diagram illustrating one embodiment of a system for providing neurostimulation.

Referring now to FIG. 2, a system 400 configured to provide neurostimulation comprises a diode 114 (e.g., a diode system) comprising a pair of electrical contacts 116 and 117. It is understood that the components shown in FIG. 2 are not drawn to scale, and that certain components may be enlarged to provide clarity in the illustration. In this embodiment, diode 114 is implanted into electrically-excitable neural tissue 120. A radio frequency exciter 130 is placed proximal to the tissue overlying diode 114 and is configured to emit a radio frequency electrical output 135. In specific embodiments, radio frequency electrical output 135 is a microwave frequency output. In particular embodiments, radio frequency electrical output 135 has a frequency between 100 MHz to 8 GHz.

During operation, radio frequency output 135 is modulated with a pulse width and rate. In specific embodiments, radio frequency output 135 is pulsed on for a time period between approximately 50 microseconds to several milliseconds. In particular embodiments, radio frequency output 135 may be pulsed between approximately once per second to two hundred times per second. This provides for a relatively low total amount of microwave energy applied to neural tissue 120.

Radio frequency output 135 is received by diode 114 and rectified so that a pulsed current flows from electrical contacts 116 and 117 sufficient to provide neurostimulation of excitable neural tissue 120. In specific embodiments, the pulsed current from electrical contacts to neural tissue 120 is between 10 microamps and 20 milliamps.

Figure 3A:
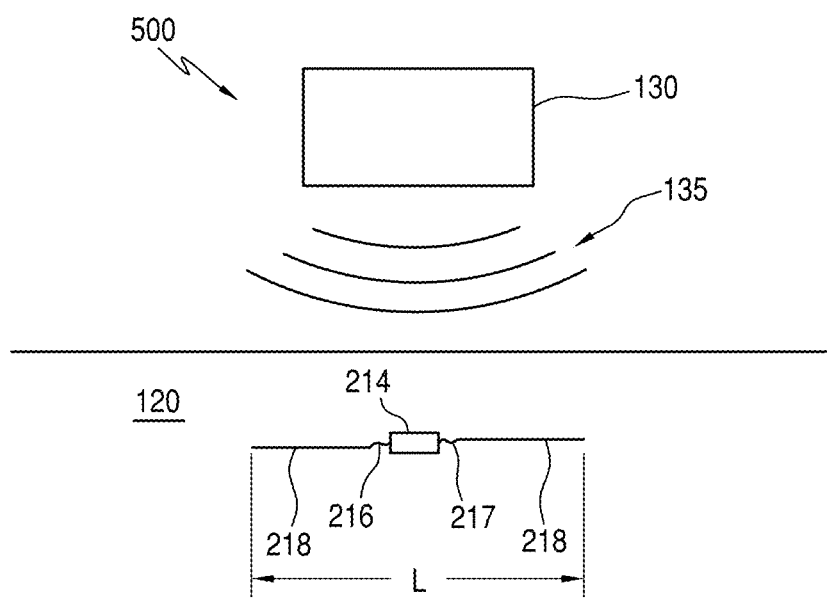
FIG. 3A is a schematic block diagram illustrating one embodiment of a system for providing neurostimulation.
Figure 3B:
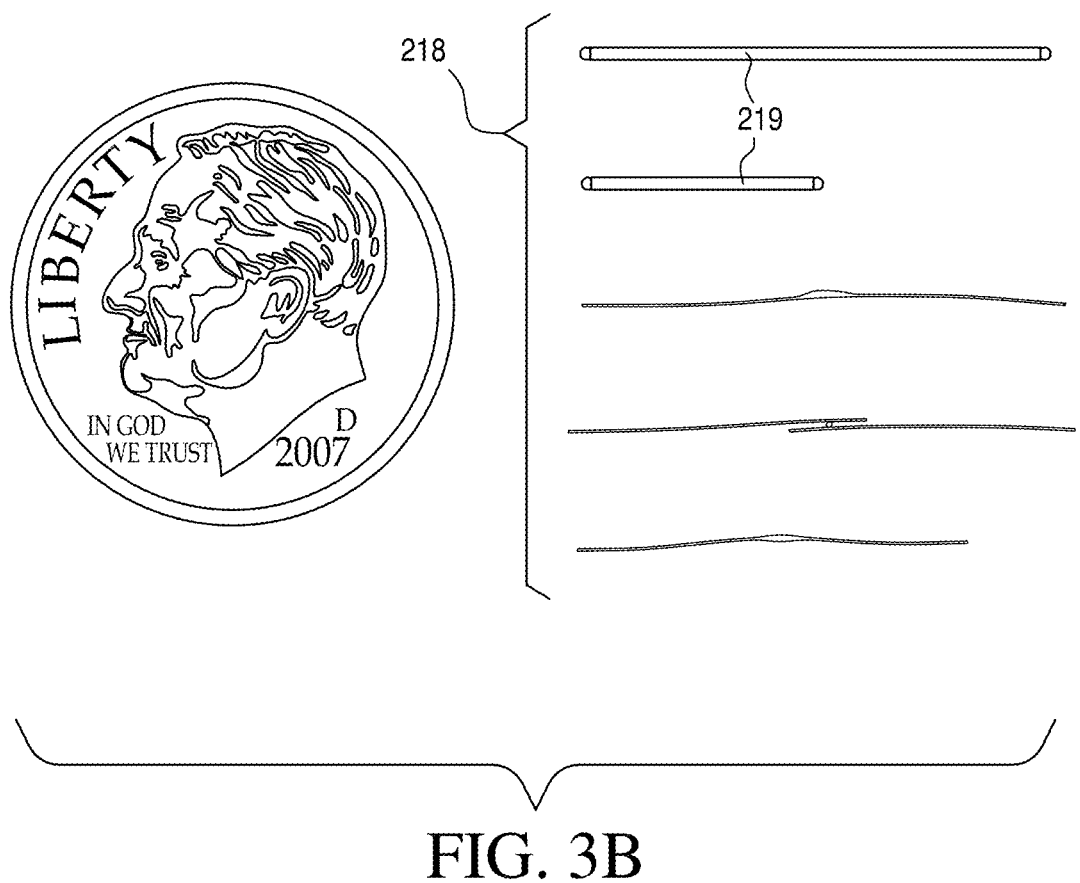
FIG. 3B is a depiction of a component of the system of FIG. 3A.

Referring now to FIG. 3A, a neurostimulation system 500 is similar to that of the previously described embodiment of FIG. 2. For example, system 500 utilizes radio frequency exciter 130 to emit a radio frequency electrical output 135. In this embodiment, however, diode electrical contacts 216 and 217 of diode 214 are coupled to a dipole 218. Dipole 218 serves as an antenna to receive radio frequency electrical output 135. In certain embodiments, dipole 218 has a length L that is between 1 millimeter and 1 centimeter. In other embodiments, dipole 218 has a length L between 1 centimeter and 5 centimeters. As shown in FIG. 3B, dipole 218 may be configured in any number of different configurations. In certain embodiments, dipole 218 may comprise an outer casing 219 that functions as a protective shell for dipole 218 and a diode.

In certain embodiments, the intensity of microwave energy applied to the body or skin can be a factor in determining the separation distances of the diode electrical contacts (e.g., electrodes). Small diode electrode spacings can have a more localized application of microwave energy and a greater energy density. There can be a trade-off in stimulation depth versus applied microwave power with decreasing diode electrode separation distances. In some embodiments, the use of high peak power in the microwave energy with low duty cycles can reduce diode threshold losses and thereby allow current to flow into the a load. If the same power was applied in a non-pulsed mode, the lower amplitude of the microwave energy would potentially be insufficient to overcome such diode barriers.

Penetration depth of the microwave energy follows well known laws to those skilled in the art. In general, microwave frequencies in the UHF range to X band (8-12 GHz) have sufficient penetration depths ranging from 10 or more centimeters to a few millimeters in tissues and are so suited for some of the embodiments.

Microwave energy applied to the body can be focused and directed by conventional techniques for using reflectors, patch antennas applied to the body such as those routinely used for therapeutic heating of the body interior at 915 MHz and 2.45 GHz, such as, for example, for treating cancer and other tissues in the body, phased array systems, double and multiple element antennas, and similar approaches. By incorporating these techniques, various embodiments are able to use less overall energy by focusing it towards the location of the implanted device.

Certain embodiments may also comprise a series of implanted diodes distributed over some volume such that they intercept a greater portion of the energy transmitted by the radio frequency exciter. In specific embodiments, the diodes can be implemented in a form factor of thin needle-like configurations with the electrical contacts disposed on either end. This configuration may allow the diodes to be inserted easily into tissues while increasing the amount of energy captured when multiple diodes are used, which may increase the amount of neurostimulation.

Further embodiments of the present invention include compact dimensions that provide benefits in installation and use of the system. For example, diodes can be manufactured in micron-order size scales by conventional photolithographic methods. In exemplary embodiments, one consideration on implant size can be the needed dipole length. For certain embodiments, the dipole length is in the range of a millimeter or so to several centimeters (e.g. between 1 centimeter and five centimeters). This length may be configured to accommodate the extent of the bioelectrical dipole stimulation length for the specific application in-vivo. In general, the higher frequencies of microwave energy, above about 1 GHz and extending to approximately 10 GHz can be more desirable for diode systems that are implanted within about several millimeters to 2 cm of the surface of the body and frequencies from approximately 300 MHz to approximately 1 GHz for device at depths greater than approximately 2 cm.

In some embodiments, the dipole and diode system can be placed within a housing such as a catheter such that it can be placed remotely within the body through a blood vessel with the catheter releasing the device for permanent placement in the body or the catheter being part of the device so that the device and/or the catheter can be permanently placed in the body.

In further embodiments, the dipole and diode system can be embodied within a silicone electrode lead, similar to a pacemaker electrode system or a neurostimulator electrode system. In these examples, the electrodes can be wireless and/or electrically powered by microwave induction to an implanted pulse generator rather than by a wired connection.

Figure 4:
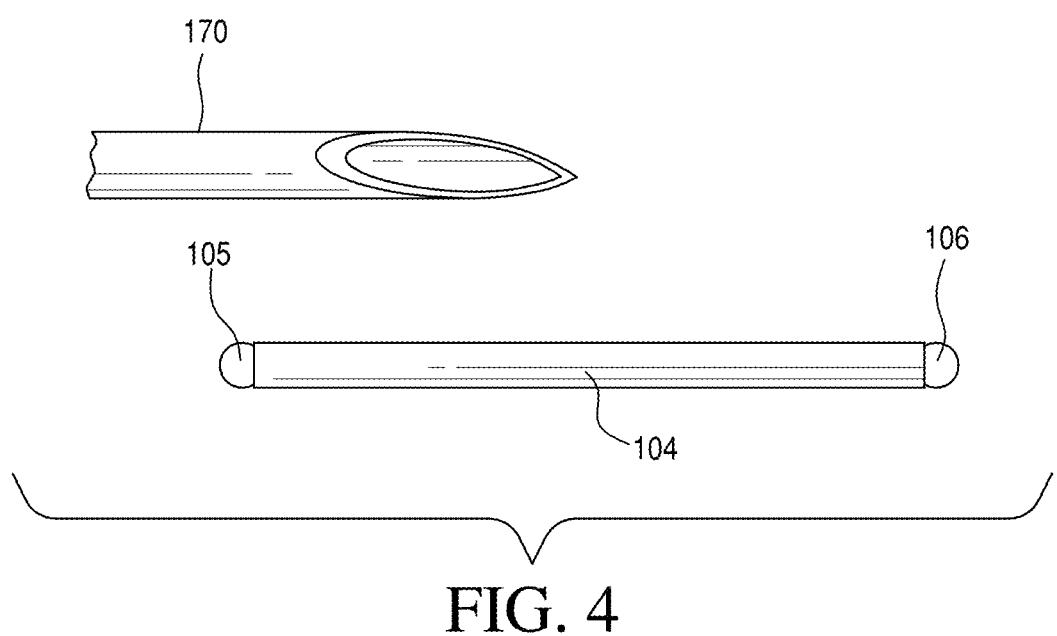
FIG. 4 is a depiction of a component used in a neurostimulation system.

Some embodiments of the present invention are reduced in physical size as compared to existing neurostimulation devices. As shown in FIG. 4, in certain embodiments, an implant 104 (which contains a diode such as diode 114 or diode 214 shown in the previous figures) is compatible with a needle 170 such as those used in common 18 gauge (or smaller) syringe used in medicine. In the embodiment shown, implant 104 also comprises a platinum electrode ball 105 at a first end of implant 104 and a platinum electrode ball 106 at a second end of implant 104.

In certain embodiments, the microwave energy applied to the body surface is generally pulsed over a relatively short interval and in the range of about 50 µs to several milliseconds and usually low duty cycles such as 10 pulses per second so that the total amount of microwave energy delivered to the body surface is relatively low. The pulse duration parameters can be defined by the needed stimulation characteristics of the neural tissue and follow well known strength-duration relationships such as those published by Reilly. The microwave pulse width and frequency in combination with the implanted diode form a system that can mimic the electrical output of a conventional wired electrical neurostimulator. In exemplary embodiments, the 1% or less pulse duty cycle means that the body tissues do not experience a thermal warming effect by application of the microwave energy to the body surface.

Figure 5:
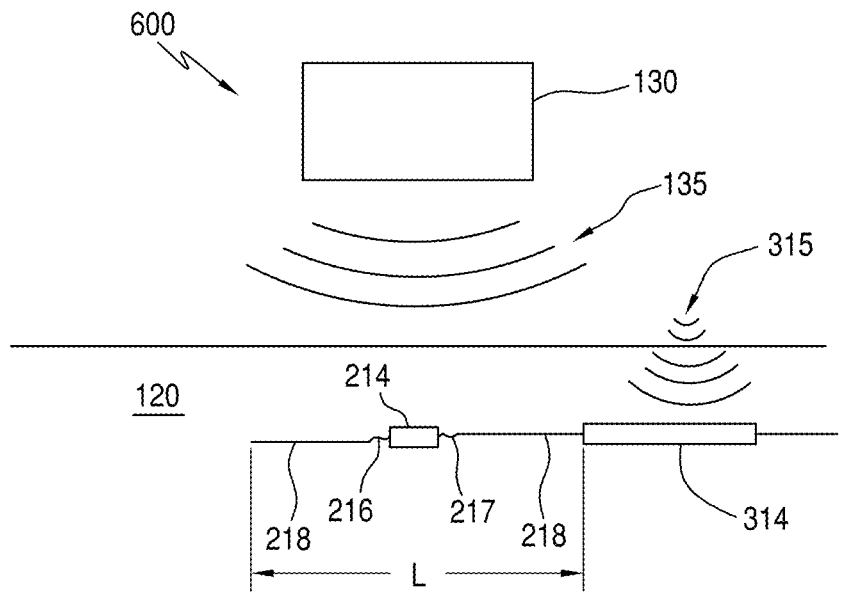
FIG. 5 is a schematic block diagram illustrating one embodiment of a system for providing neurostimulation.

In certain embodiments, the diode or diodes are placed in series or parallel with a microminiature electrical switch. In specific embodiments, the switch comprises a polymer material loaded with a finely dispersed particulate conductive phase. In such embodiments, this polymer material permits the process of electronic conduction by electron hopping (also known as percolation) that occurs when a sufficient number of conductive particles are close enough to permit electronic tunneling through the intermediate distance of insulator. Small changes in particle distance spacing by the passage of a pressure wave can effectively causes a change in the resistance of the polymer and thus accomplish the function of a switch. Referring now to FIG. 5, a system 600 comprises an implanted electrical switch 314 coupled to diode 214. Switch 314 may be configured to be activated by an acoustic pressure wave 315, so that when switch 314 is activated, diode 214 will conduct an electrical current. In other respects, system 600 is equivalent to system 500 described previously. Accordingly, other aspects of the operation of system 600 will not be described in detail.

When sound energy impacts this composite device, the resistance of the switch falls due to a pressure response and enables current to flow through the diode. This approach allows selectivity of neurostimulation between a number of diodes implanted in tissue by way of timing the electrode electrical current flow to the arrival of the sound at the diode location.

Likewise the sensitivity of a diode can be switched on and off momentarily by the passage of an acoustic pressure wave using a percolating particulate polymer. The insulating polymer can have properties of substantial resistance to the fluid medium in which it is used. This form of pressure transducer has the advantages that it can be made in very thin layers and can be disposed on a substrate by commercial processes of photolithography and batch fabrications. It has a relatively large change in current flow with pressure and can be used with small exposed polymer areas and so lending itself to miniaturized sensors.

Embodiments utilizing multiple diodes can be utilized to perform various functions. For example, recording of the spontaneous activity of the nervous system is of high interest in the design of neuroprostheses and in creating effective methods of using electrical stimulation to replace lost function. The creation of man-machine interfaces requires ways of detecting neural activity of the body as well as stimulating it. Thus, there is interest in designing systems that not only stimulate excitable tissue but record from it and that then can provide a function of telemetry of signals from within the body to the skin surface where they can be telemetered to a remote location.

In certain embodiments, locating or implanting semiconductor diodes near electrically active neural tissues can provide a telemetry function. This function can allow a recording of the bioelectrical events in body tissue by recording and demodulating signals that result from the interaction of bioelectrical currents with a high frequency driven carrier current passing through a semiconductor diode whose leads contact tissue.

The human body can be electrically modeled as a volume conducting medium. Natural or artificial current sources in the interior of the body will thereby produce volume potentials. Bioelectrical currents flowing in excitable tissue in the body are generally modeled as current sources in the range of tens to hundreds of microamperes and with associated electric fields in the range of microvolts to tens of millivolts in the case of transmembrane potentials. These devices can be understood from volume conductor propagation of a small dipolar current source in tissue that follows well understood rules. The potential V appears on the skin surface as:

$$V = id \cos\theta / 4\pi\sigma r^2$$

Where i is the current flow over a dipole length d, $\sigma$ is the medium conductivity, and r is the distance from the center of the dipole to the skin surface. Thus there is a square law loss of the signal strength generated by the current source at depth from the body surface and there is a vector relationship to orientation of the electrode pairs.

An unexpected principle noted in exemplary embodiments of the present invention is that low level bioelectrical events can alter the characteristics of RF semiconductor junction diodes in a way that is remotely detectable without the necessary use of biopotential preamplification.

The characteristics of p-n junction diodes, such as those that may be suitable for diode 114 or 214 in previously-described embodiments, can be substantially varied in their characteristics by biopotentials when reverse biased or when biased near their turn-on threshold. Parameters such as junction capacitance, effective resistance, and nonlinear second harmonic production can all be substantially affected by submillivolt level electrical signals applied to them.

Figure 6:
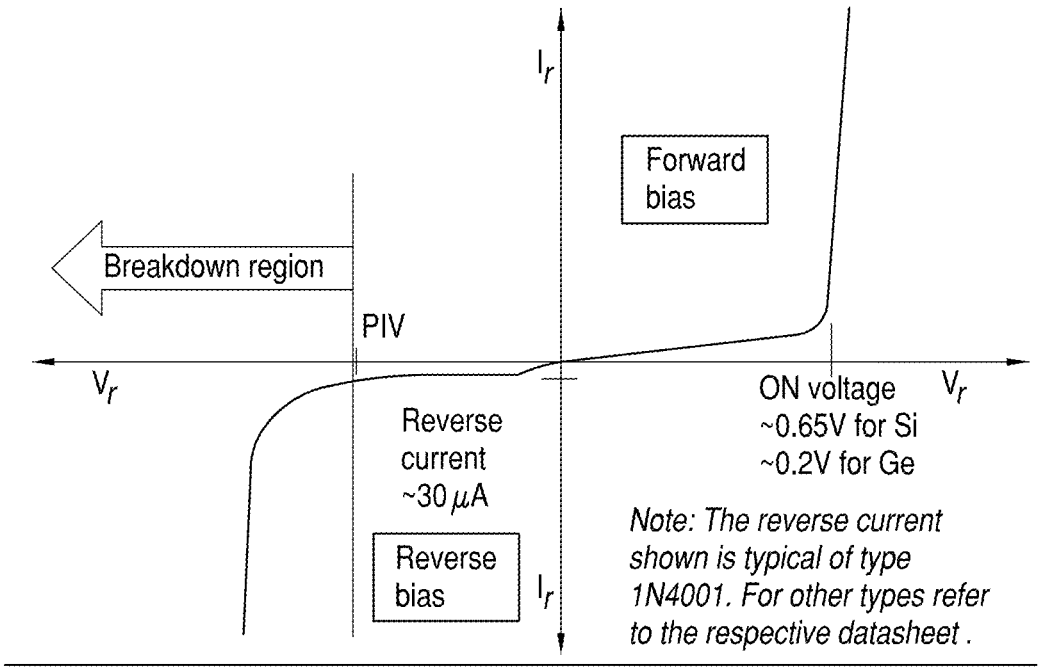
FIG. 6 is a graph illustrating a voltage response of a diode in accordance with the present embodiments.

This process can be conceived as the diode acting as a (nonlinear) multiplying element. The Shockley equation shows the relationship of the diode forward current to an applied bias voltage.

$$I=I_S(e^{V_D/(nV_T)}-1)$$

where I is the diode current, $I_S$ is a scale factor called the saturation current, $V_D$ is the voltage across the diode, $V_T$ is the thermal voltage, and n is the emission coefficient. FIG. 6 shows the sharp knee in the i-v curve near on threshold. By operating $V_D$ slightly below this point (which moves towards the origin in zero-bias type Shottky diodes) millivolt biopotential signals can amplitude modulate an externally applied and relatively high frequency carrier current also passing through the diode. This process is known as mixing or sometimes as intermodulation when applied to the design of radio devices. This process may be performed using high performance low-noise mixer diodes, such as those that are routinely used in RF communications at microvolt signal levels. Accordingly, in such an embodiment, the mixing process may not be a significant source of noise or limitation on the biopotential intermodulation process.

Figure 7:
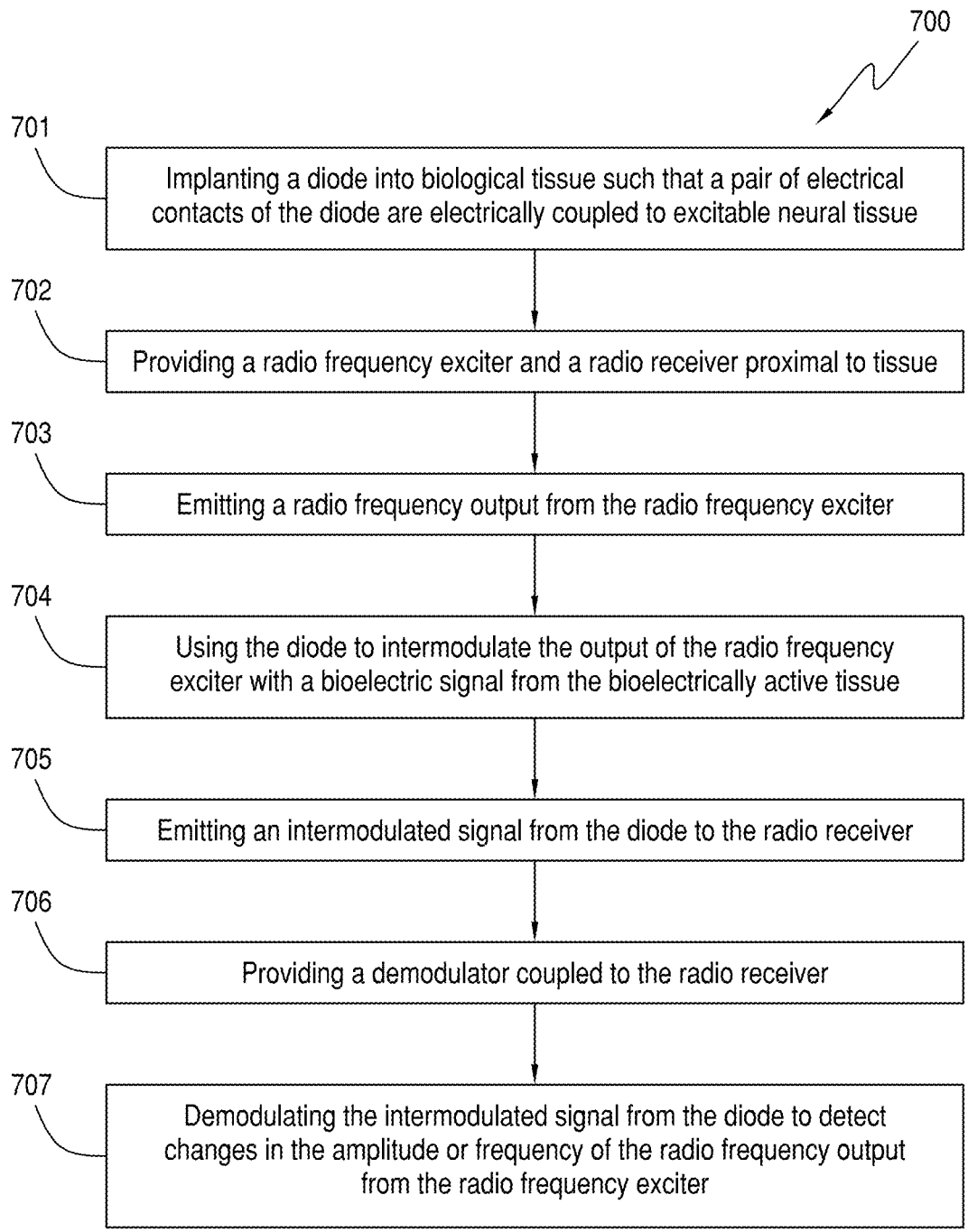
FIG. 7 is schematic flowchart diagram illustrating one embodiment of a method for providing neurotelemetry.

Referring now to FIG. 7, an exemplary method 700 of providing neurotelemetry from biological tissues is shown, according to an embodiment. This embodiment is not limiting. Other embodiments may comprise different combinations of the individual features shown and described in FIG. 7 or may comprise the features in a different order than that shown in FIG. 7.

The exemplary embodiment illustrated in method 700 can comprise activity 701 of implanting a diode proximal to bioelectrically active tissue and activity 702 of providing a radio frequency exciter and a radio receiver proximal to tissue overlying the diode. Method 700 further can comprise activity 703 of emitting a radio frequency output from the radio frequency exciter to the diode and activity 704 of using the diode to intermodulate the output of the radio frequency exciter with a bioelectric signal from the bioelectrically active tissue. Method 700 additionally can comprise activity 705 of emitting an intermodulated signal from the diode to the radio receiver and activity 706 of providing a demodulator coupled to the radio receiver. Furthermore, method 700 can comprise activity 707 of demodulating the intermodulated signal from the diode to detect changes in the amplitude or frequency of the radio frequency output from the radio frequency exciter.

Figure 8:
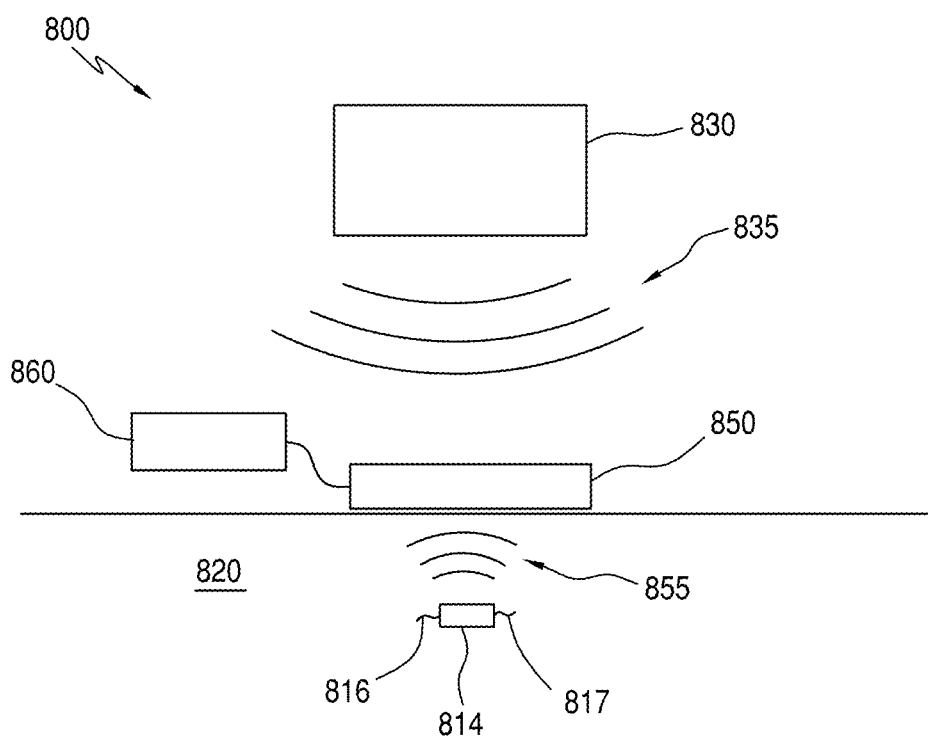
FIG. 8 is a schematic block diagram illustrating one embodiment of a system for providing neurotelemetry.

Referring now to FIG. 8, a system 800 configured to provide neurotelemetry comprises a diode 814 comprising a pair of electrical contacts 816 and 817. It is understood that the components shown in FIG. 8 are not drawn to scale, and that certain components may be enlarged to provide clarity in the illustration. In this embodiment, diode 814 is implanted into electrically-excitable neural tissue 820. A radio frequency exciter 830 is placed proximal to the tissue overlying diode 814 and is configured to emit a radio frequency electrical output 835.

During operation, radio frequency output 835 is modulated with a pulse width and rate. In addition, diode 814 is configured to intermodulate the output of the radio frequency exciter with a bioelectric signal from electrically-excitable neural tissue 820. Diode 814 is further configured to emit an intermodulated signal 855 to a radio receiver 850. System 800 further comprises a demodulator 860 coupled to radio receiver 850. Furthermore, demodulator 860 is configured to demodulate intermodulated signal 855 from diode 814 to detect changes in the amplitude or frequency of radio frequency output 835 from the radio frequency exciter 830.

In certain embodiments, a high frequency signal is applied to the diode from an external RF source constituting a carrier current. Bioelectric currents in parallel with the mixer diode amplitude modulate the applied RF carrier current excitation. When placed in tissue, volume conductivity carries the biopotential modulated carrier current to the surface where it is detected by a second set of surface bioelectrodes or antenna. Demodulation of the detected signal reproduces the original biopotential waveform.

The implanted diode assembly can therefore intermodulate the bioelectrical event on a superimposed high frequency carrier. Over a small change in biopotential, the changes in the carrier current through the diode is reasonably linear. At low drive levels, the diode presents a relatively high source impedance to the electrodes.

In many types of neural monitoring applications, there is a need for multichannel operation to cope with the complexity of functionality of the body. Large electrode arrays systems involving fine wires are used to penetrate tissue to stimulate patterns of neural response particularly in the brain, eye, and auditory prostheses.

It is noted that using a lower amplitude of microwave, instead of applying a relatively strong source of microwave radiation to the implant site, causes the diode to act differently. Microwave currents driven through tissues combine with the natural ionic currents flowing in tissue and do not stimulate tissues by its electrical current flow, but rather intermodulates with local tissue biopotentials at the diode.

The passage of a small but high frequency electrical current flow induced in tissue from an external source combined with a demodulation process on the re-radiated frequencies created by the intermodulation process with the diode, allows one to reconstruct the waveform of the original bioelectrical event that was flowing locally in the tissue and present electrically across the diode-tissue contacts. By demodulating intermodulation components as is known in radio communications, a user is able to remotely record the modulating biopotential signal amplitude.

This approach may provide an improvement over methods in the prior art which use resonant circuits coupled with varactor diodes or other voltage sensing devices of varying sorts. One advantage may be an increased ability to miniaturize the implanted device.

Specific embodiments comprise the use of multiple diodes of micrometer-order in size by conventional methods of semiconductor manufacturing. In specific embodiments, the diodes can be introduced into a host by way of a carrier fluid, which can allow the diodes to be distributed more easily through a larger volume of a tissue or at specific points where the diodes are placed. Diodes which are aligned with the electric current flow will forward conduct on one phase of the AC cycle and be passive on the next phase. While it may be desirable for efficiency to have all of the diodes aligned in a common direction, it is not a requirement as long as a sufficient fraction are aligned to produce a sufficiently strong rectification of the current flow. Alignment of the diodes can be achieved by multiple methods such as by providing and/or constructing the diodes with magnetic materials and magnetizing the diodes to be aligned in a polar magnetic field.

In certain embodiments, the functionality of a diode can be achieved in multiple ways including that of the use of commercially available semiconductor diodes. Other embodiments may comprise diodes created using microscopic combinations of two different metals separated by a thin insulating layer. Such configurations may be accomplished, for example, by silver copper-oxide copper layering as known to those skilled in the art. Other embodiments may comprise silver and its chloride in combination with other less reactive metals such as platinum or gold. Such diodes can be made essentially any size including as a fine dispersion in a biocompatible fluid transfer medium. Similar diode effects can be achieved using organic semiconductors. In particular, it is known that the organic polypyrrole is an electrical semiconductor, and when doped by various ions, it acquires either p-type or n-type characteristics. A diode can therefore be formed by the junction of organic materials. In various embodiments, these diodes can be fabricated in accordance with manufacturing processes that permit them to operate at high microwave frequencies.

As before, it will be apparent to those skilled in the art that detection and demodulation of both the fundamental as well as harmonics of the carrier wave are possible in a process to demodulate the bioelectric waveform.

It is noted that the efficiency of the diode in intermodulating the carrier wave with the bioelectrical events is determined by the specific characteristics of the diode. Zero bias Shottky diodes for example, require no DC bias offset in their operation while other diodes may require DC bias of varying degrees depending on their manufacture.

Depending on the selection of the diode and its electrical characteristics, it is possible to be somewhat selective as to which of a series of diodes introduced at varying depths in tissue contribute to the detected intermodulation of the applied carrier by way of observing that there is an optimum dc bias which produces the greatest possible intermodulation. If the dc bias level is either too high or too low, the intermodulation of a given diode will be relatively little. A series of diodes disposed within tissue for example, can be somewhat individually addressed and their contribution to the overall demodulated signal maximized by applying a DC bias level to the skin along with the carrier frequency. Diodes at some middle position in the tissue will receive an optimal DC bias due to the attenuation of the bias level with depth and so providing an optimum electrical operating condition at that point. Likewise if the bias level is ramped over time there may be a sequential reading the diodes relative to their increasing position of depth in the tissue.

The basic electronic design employs an unusually different approach to energy transfer to miniature medical bioelectronic implants as compared to the current art. High frequency (GHz microwave range) electric fields can be shown to interact in unexpected ways with simple semiconductor diode chips when they are placed near or within biologically-excitable tissues.

The design principle allows simple wireless transmission of electrical energy over short ranges to an implanted chip to the extent that it can produce therapeutic neurostimulation. Some embodiments of the invention also excite the same implanted chip so that it acts as a transmitter and thus provides telemetry of bioelectrical and sensor signals from tissues. One embodiment is a compact cell-phone like receiver placed near the skin surface.

Thus, various embodiments provide a method and design that can do the complementary tasks of both neurostimulation and neurorecording. Further embodiments allow a substantial reduction in the complexity, size, and bulk of implanted microelectronic neurostimulation/neurotelemetry devices to the degree where some prototypes fit through the lumen of common syringe needles.

Figure 9:
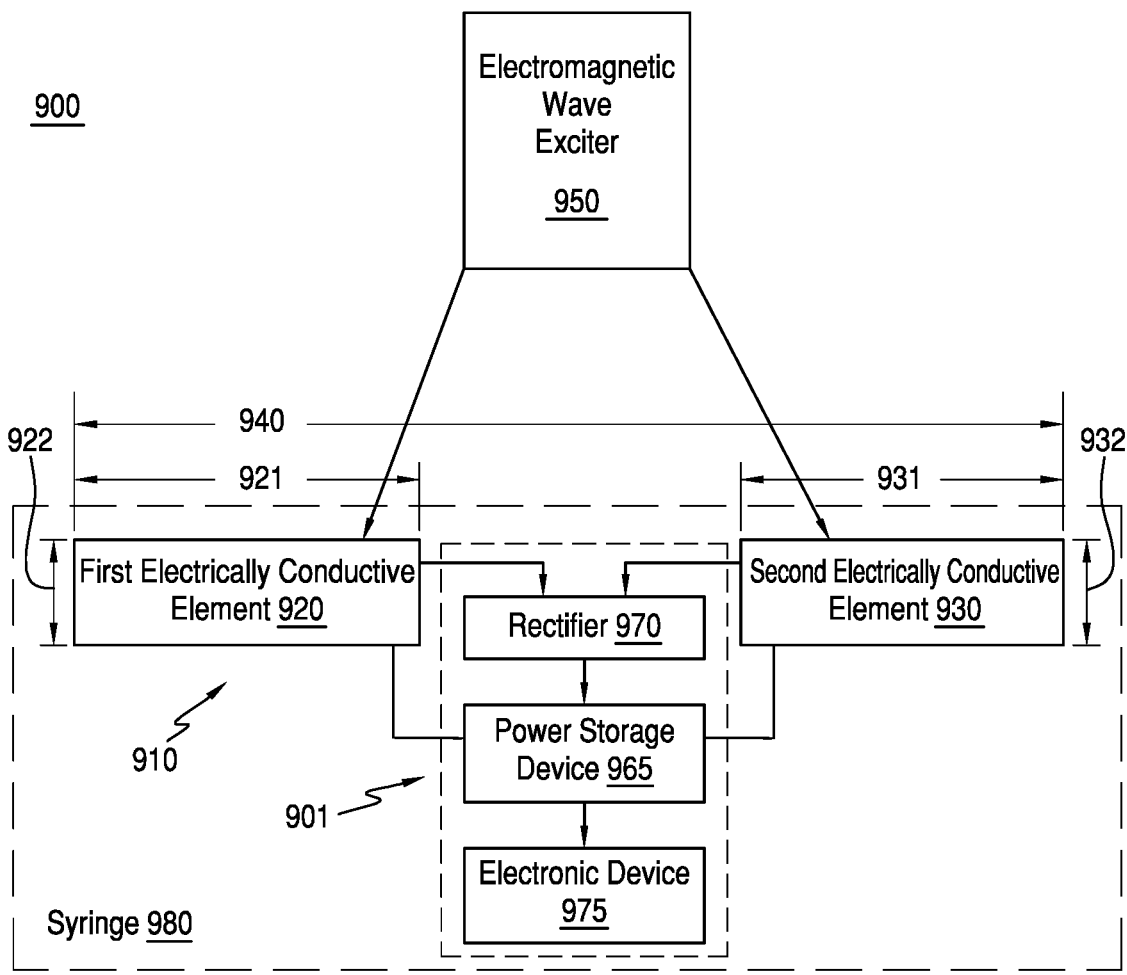
FIG. 9 is a schematic block diagram illustrating one embodiment of another apparatus.

Referring now back to the drawings, FIG. 9 illustrates an apparatus 900, according to a first embodiment of apparatus 900. Apparatus 900 is merely exemplary and is not limited to the embodiments presented herein. Apparatus 900 can be employed in many different embodiments or examples not specifically depicted or described herein.

Referring now to FIG. 9, in many embodiments, apparatus 900 can comprise electronic device 901, and electronic device 901 can comprise dipolar antenna 910. In the same or different embodiments, dipolar antenna 910 can comprise first electrically conductive element 920. In the same or different embodiments, first electrically conductive element 920 can comprise first length 921 and first width 922. In the same or different embodiments, dipolar antenna 910 can comprise second electrically conductive element 930. In the same or different embodiments, second electrically conductive element 930 can comprise second length 931 and second width 932. In many embodiments, first electrically conductive element 920 can be similar to second electrically conductive element 930. In other embodiments, first electrically conductive element 920 and second electrically conductive element 930 can be different from each other.

Referring back to FIG. 9, in the same or different embodiments, dipolar antenna 910 can be configured to be implanted in biological tissue. In many embodiments, biological tissue can comprise human biological tissue. In some embodiments, biological tissue can comprise brain tissue, muscle tissue, and/or nervous system tissue. In the same or different embodiments, biological tissue can comprise biological tissue other than human biological tissue (e.g., biological tissue of an animal). In the same or different embodiments, dipolar antenna 910 can be configured to be implanted as deep as approximately 10-15 centimeters into the biological tissue. In other embodiments, dipolar antenna 910 can be configured to be implanted just below a surface of the biological tissue.

In the same or different embodiments, dipolar antenna 910 can comprise to receive a dipolar electric field. In the same or different embodiments, dipolar antenna 910 can be configured to receive a dipolar magnetic field. In many embodiments, when dipolar antenna 910 is configured to receive a dipolar electric field and/or a dipolar magnetic field, energy transferred from the dipolar magnetic field to dipolar antenna 910 can be considerably less and/or negligible compared to the energy transferred to dipolar antenna 910 from the dipolar electric field. In other embodiments, the energy transferred from the dipolar magnetic field may not be considerably less and/or negligible compared to the energy transferred from the dipolar electric field.

Referring back to FIG. 9, in the same or different embodiments, dipolar antenna can comprise combined length 940 of first length 921 and second length 931, and combined length 940 can be greater than or equal to approximately 2 millimeters and less than or equal to approximately 6 centimeters. In the same or different embodiments, combined length 940 can be greater than or equal to approximately 5 millimeters and less than or equal to approximately 5 centimeters. In still further embodiments, combined length 940 can be approximately 0.5 millimeters to 2 centimeters for applications near the body surface such as for peripheral nerve stimulation, and can be up to approximately 5 centimeters for devices implanted deep within the body. Although resonance of the dipolar antenna to the applied microwave frequency can improve coupling, satisfactory results can also be achieved with untuned dipolar elements of varying lengths suitable for the particular application.

In the same or different embodiments, each of first width 922 and/or second width 932 can be less than or equal to approximately 1.5 millimeters. In the same or different embodiments, each of first width 922 and/or second width 932 can be less than or equal to approximately 1.3 millimeters, approximately 1.2 millimeters, approximately 1.1 millimeters, approximately 1.0 millimeters, approximately 0.8 millimeters, approximately 0.6 millimeters, approximately 0.5 millimeters, or approximately 0.4 millimeters. In many embodiments, the antenna width in part defines the resistance of the antenna to radiation. Fine wires having 20-100 micron diameters can provide a good balance between sufficiently small size and low resistance to adequately act as an antenna.

Referring back to FIG. 9, in many embodiments, apparatus 900 can comprise electromagnetic wave exciter 950. In the same or different embodiments, electromagnetic wave exciter 950 can be configured to emit electromagnetic radiation. In the same or different embodiments, the electromagnetic radiation can comprise radio frequency electromagnetic radiation. In other embodiments, the electromagnetic radiation can comprise microwave frequency electromagnetic radiation. In many embodiments, electromagnetic wave exciter 950 can be separate from dipolar antenna 910 and/or electronic device 960, energy storage device 965, rectifier 970, and/or syringe 980, each of which is described below. In some examples, energy storage device 965 can also be referred to as a power storage device.

In the same or different embodiments, the electromagnetic radiation can comprise the dipolar electric field. In the same or different embodiments, the electromagnetic radiation can comprise the dipolar magnetic field. In the same or different embodiments, apparatus 900 can be configured to transfer energy between electromagnetic wave exciter 950 and dipolar antenna 910 through the dipolar electric field of the electromagnetic radiation. In many embodiments, electromagnetic wave exciter 950 can be electrically coupled to an energy source (e.g., a battery). Losses in power received by the dipolar antenna resulting due to non-optimal coupling can be overcome by increasing the power of electromagnetic radiation and/or by adjusting the proximity of electromagnetic wave exciter 950 to dipolar antenna 910. In many embodiments, reducing the distance between electromagnetic wave exciter 950 and dipolar antenna 910 can decrease such power losses. As a result, dipolar antenna 910 can be made small and/or compact even where dipolar antenna 910 is not optimally designed.

In the same or different embodiments, electromagnetic wave exciter 950 can comprise an additional dipolar antenna. In some embodiments, electromagnetic wave exciter 950 can comprise any other conventional compact microwave antenna (e.g., a patch antenna). Microwave strip antennas and/or patch antennas can be convenient for application to the surface of a body because they can be conformal with skin and/or clothing.

In many embodiments, first electrically conductive element 920 can be approximately co-linear with second electrically conductive element 930. In the same or different embodiments, dipolar antenna 910 can be oriented approximately parallel to electromagnetic wave exciter 950. In other embodiments, dipolar antenna 910 can be oriented other than parallel to electromagnetic wave exciter 950.

In many embodiments, the electromagnetic radiation can comprise a peak power level. In the same or different embodiments, the electromagnetic radiation can comprise an average power level. In the same or different embodiments, the peak power level can be greater than or equal to approximately 50 watts and less than or equal to approximately 100 watts. In the same or different embodiments, the average power level can be greater than or equal to approximately 1 watt and less than or equal to approximately 10 watts. In other embodiments, the peak power level can be greater than or equal to approximately 10 watts and less than or equal to approximately 300 watts.

In many embodiments, electromagnetic wave exciter 950 can be configured such that the electromagnetic radiation can be controlled in frequency, amplitude (e.g., intensity), and/or modulation. In the same or different embodiments, electromagnetic wave exciter 950 can be configured to pulse and/or burst the electromagnetic radiation to minimize the specific absorption rate of energy applied to the skin. The specific absorption rate is a measurement of the rate at which energy is absorbed by the body when exposed to a radio frequency electromagnetic field. Specific absorption rate is defined as the power absorbed per mass of tissue and can have units of watts per kilogram (W/kg). In the United States, the Federal Communications Commission (FCC) is generally responsible for regulating the acceptable specific absorption rates emitted by electronic devices. For example, the FCC limits the specific absorption rate of telephones to 1.6 W/kg or less.

Applying energy in pulses and/or bursts can help overcome any diode forward threshold voltage while the lowered duty cycle then reduces the total energy applied to be consistent with the acceptable specific absorption rate level. In some embodiments, a duty cycle of approximately 1-10% on the transmitter burst can be consistent with optimizing the transfer of energy to dipolar antenna 910. Duty cycles can be arranged for optimal energy transfer based on the thermal characteristics of the tissue and the ability of the tissue to dissipate heat over short millisecond order intervals of time. In various embodiments, if the rectified energy induced is intended to provide neurostimulation, the energy can be pulsed and/or bursted in a manner consistent with the corresponding physiological requirements to provide such neurostimulation. For example, for an "on time" of approximately 50 microseconds to 1 millisecond, typical neurostimulation could be a pulse repetition rate of approximately 0.5 Hertz to 2,000 Hertz, as consistent with a duty cycle that is defined by a desired specific rate of absorption limit. In another neurostimulation example, the pulse repetition rate could be approximately 1 Hertz to 1,000 Hertz. For other energy transfer purposes, the pulse characteristics can be the same or varied depending on the needs of the energy storage system. For example, for a time period of greater than or equal to approximately 1 microsecond and less than or equal to approximately 10 milliseconds, the pulse frequency can be greater than or equal to approximately 0.5 pulses per second and less than or equal to approximately 2000 pulses per second.

Referring back to FIG. 9, in many embodiments, electronic device 901 can comprise electronic device 960. In the same or different embodiments, electronic device 960 can comprise energy storage device 965 electrically coupled to dipolar antenna 910. In the same or different embodiments, apparatus 900 can be configured to provide energy from dipolar antenna 910 to electronic device 960 and/or energy storage device 965 electrically coupled to electronic device 960.

In the same or different embodiments, electronic device 960 can comprise electronic device 975 electrically coupled to energy storage device 965. Electronic device 975 can comprise a bioelectronic medical sensor, a transducer, a communication system, and/or an actuator, etc. In the same or different embodiments, any of the bioelectronic medical sensor, the transducer, the communication system, and/or the actuator can be similar to any conventionally used bioelectronic medical sensor, transducer, communication system, and/or actuator, respectively (e.g., any bioelectronic medical sensor, transducer, communication system, and/or actuator having millimeter or sub-millimeter dimensions), and can include a microcontroller. In the same or different embodiments, energy storage device 965 can comprise a battery. In the same or different embodiments, energy storage device 965 can be similar to any conventionally used battery (e.g., any battery conventionally used with millimeter/sub-millimeter devices). In the same or different embodiments, energy storage device 965 can comprise a capacitor.

Referring back to FIG. 9, in many embodiments, electronic device 960 can comprise rectifier 970 electrically coupled to dipolar antenna 910 and energy storage device 965. In the same or different embodiments, rectifier 970 can comprise a diode and/or a microcontroller. In other embodiments, rectifier 970 can comprise multiple diodes. In the same or different embodiments, the multiple diodes can be electrically coupled in series (e.g., as a bridge rectifier), in parallel, or in some combination of the two. In various embodiments, the diode can comprise a Shottky diode. In the same or different embodiments, the diode can be similar to diode 114 (FIG. 2), as described above.

In many embodiments, dipolar antenna 910 can be devoid of an inductive coil. In the same or different embodiments, electromagnetic wave exciter 950 can be devoid of an inductive coil. In the same or different embodiments, apparatus 900 can be devoid of an inductive coil.

In many embodiments, the electromagnetic radiation can have a frequency greater than or equal to approximately 300 Megahertz and less than or equal to approximately 30 Gigahertz. In some embodiments, the electromagnetic radiation can have a frequency of approximately 915 Megahertz. In further embodiments, the electromagnetic radiation can have a frequency of approximately 2.45 Gigahertz.

In many embodiments, first electrically conductive element 920 and/or second electrically conductive element 930 can comprise a biocompatible material. In the same or different embodiments, the biocompatible material can comprise platinum, tungsten, palladium, and/or gold. In the same or different embodiments, the biocompatible material can comprise at least one of any other noble metal. In some embodiments, first electrically conductive element 920 and second electrically conductive element 930 can comprise different ones of the biocompatible materials. In some embodiments, first electrically conductive element 920 and/or second electrically conductive element 930 can comprise a semiconductor or insulator (e.g., silicon, alumina, etc.) packed with a conductive power (e.g., carbon fiber).

In many embodiments, first electrically conductive element 920 and/or second electrically conductive element 930 can comprise an electrically insulating outer layer. In the same or different embodiments, the insulating outer layer can comprise a biocompatible polymer. In the same or different embodiments, the insulating outer layer can cover all or part of first electrically conductive element 920 and/or second electrically conductive element 930. In the same or different embodiments, the insulating outer layer does not cover at least one or more parts of first electrically conductive element 920 and/or second electrically conductive element 930.

Referring now to FIG. 9, apparatus 900 can comprise syringe 980, wherein electronic device 901 (including dipolar antenna 910 and electronic device 960) is located within syringe 980. In many embodiments, electronic device 901 can be configured to pass through a lumen of a 14 gauge needle, a 15 gauge needle, a 16 gauge needle, a 17 gauge needle, an 18 gauge needle, a 19 gauge needle, a 20 gauge needle, a 21 gauge needle, and/or a 22 gauge needle of a syringe. In the same or different embodiments, the lumen can be similar to needle 170 (FIG. 4).

In many embodiments, none of, part of, or all of electronic device 901 can be hermetically sealed. In the same or different embodiments, none of, part of, or all of electronic device 901 can be non-corrosive.

Figure 10:
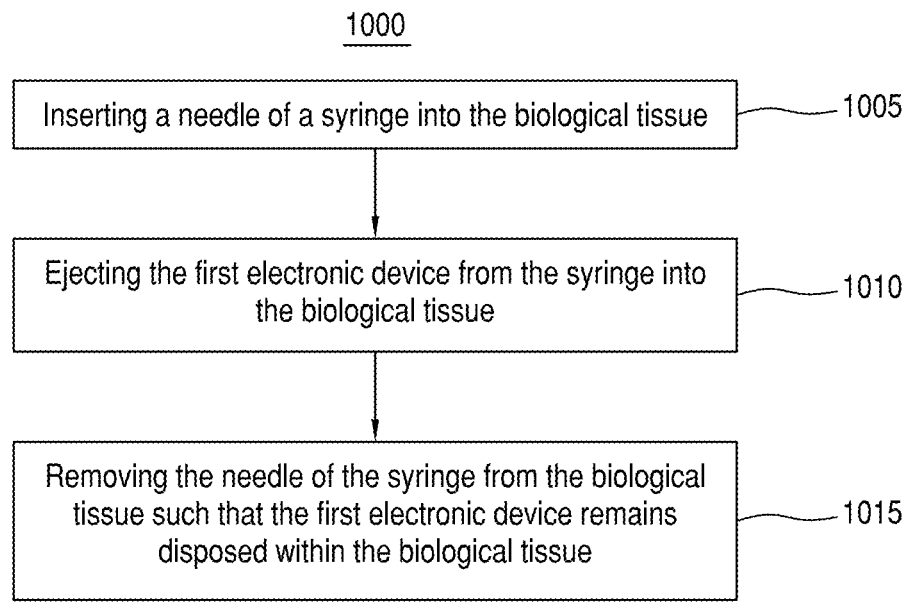
FIG. 10 illustrates a flow chart for an embodiment of a method of implanting a first electronic device into biological tissue.

Returning once again to the drawings, FIG. 10 illustrates a flow chart for an embodiment of a method 1000 of implanting a first electronic device into biological tissue. Method 1000 is merely exemplary and is not limited to the embodiments presented herein. Method 1000 can be employed in many different embodiments or examples not specifically depicted or described herein. In some embodiments, the procedures, the processes, and/or the activities of method 1000 can be performed in the order presented. In other embodiments, the procedures, the processes, and/or the activities of method 1000 can be performed in any other suitable order. In still other embodiments, one or more of the procedures, the processes, and/or the activities of method 1000 can be combined or skipped.

Referring to FIG. 10, in many embodiments, method 1000 can comprise procedure 1005 of inserting a needle of a syringe into the biological tissue. In the same or different embodiments, procedure 1005 can comprise inserting a needle of a syringe into the biological tissue to a depth within a few centimeters of a surface of the biological tissue. In other embodiments, procedure 1005 can comprise inserting a needle of a syringe into the biological tissue to a depth of approximately 10-15 centimeters of the surface of the biological tissue. In the same or different embodiments, the syringe can be similar to syringe 980 (FIG. 9), as described above.

In the same or different embodiments, the syringe can contain the first electronic device. In the same or different embodiments, the first electronic device can be similar to at least part of apparatus 900 (FIG. 9), as described above. In the same or different embodiments, the first electronic device can comprise an electronic device such as electronic device 901 and/or a dipolar antenna similar to dipolar 910 (FIG. 9), as described above. In the same or different embodiments, the dipolar antenna can further comprise a first electrically conductive element having a first end and a second electrically conductive element having a second end.

In the same or different embodiments, the first electronic device can further comprise a second electronic device and/or an energy storage device electrically coupled to the second electronic device. In the same or different embodiments, the second electronic device can be similar to electronic device 960 (FIG. 9), as described above. In the same or different embodiments, the energy storage device can be similar to energy storage device 965 (FIG. 9), as described above. In many embodiments, the first end and the second end of the dipolar antenna are electrically coupled to the second electronic device and/or the energy storage device electrically coupled to the second electronic device to permit the dipolar antenna to provide a current to the second electronic device. In some examples, the second electronic device can be tissue stimulating electrodes coupled with tissue and configured to provide an electrical impetus to the tissue.

Referring again to FIG. 10, in many embodiments, method 1000 can comprise procedure 1010 of ejecting the first electronic device from the syringe into the biological tissue. In the same or different embodiments, the biological tissue can be similar to the biological tissue of apparatus 900 (FIG. 9), as described above. Referring again to FIG. 10, in many embodiments, method 1000 can comprise procedure 1015 of removing the needle of the syringe from the biological tissue such that the first electronic device remains disposed within the biological tissue.

Figure 11:
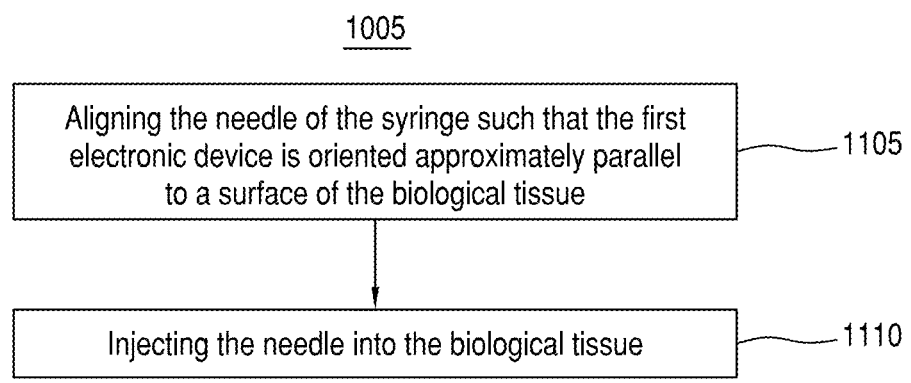
FIG. 11 illustrates a flow chart for an embodiment of a procedure of inserting a needle of a syringe into the biological tissue of the method of FIG. 10.

Referring now to FIG. 11, in many embodiments, procedure 1005 (FIG. 10) of inserting a needle of a syringe into the biological tissue can comprise a process 1105 of aligning the needle of the syringe such that the first electronic device is oriented approximately parallel to a surface of the biological tissue. In the same or different embodiments, the procedure 1005 (FIG. 10) can comprise aligning the needle of the syringe such that the first electronic device is oriented other than approximately parallel to a surface of the biological tissue. In the same or different embodiments, procedure 1005 (FIG. 10) can further comprise a process 1110 of injecting the needle into the biological tissue.

Figure 12:
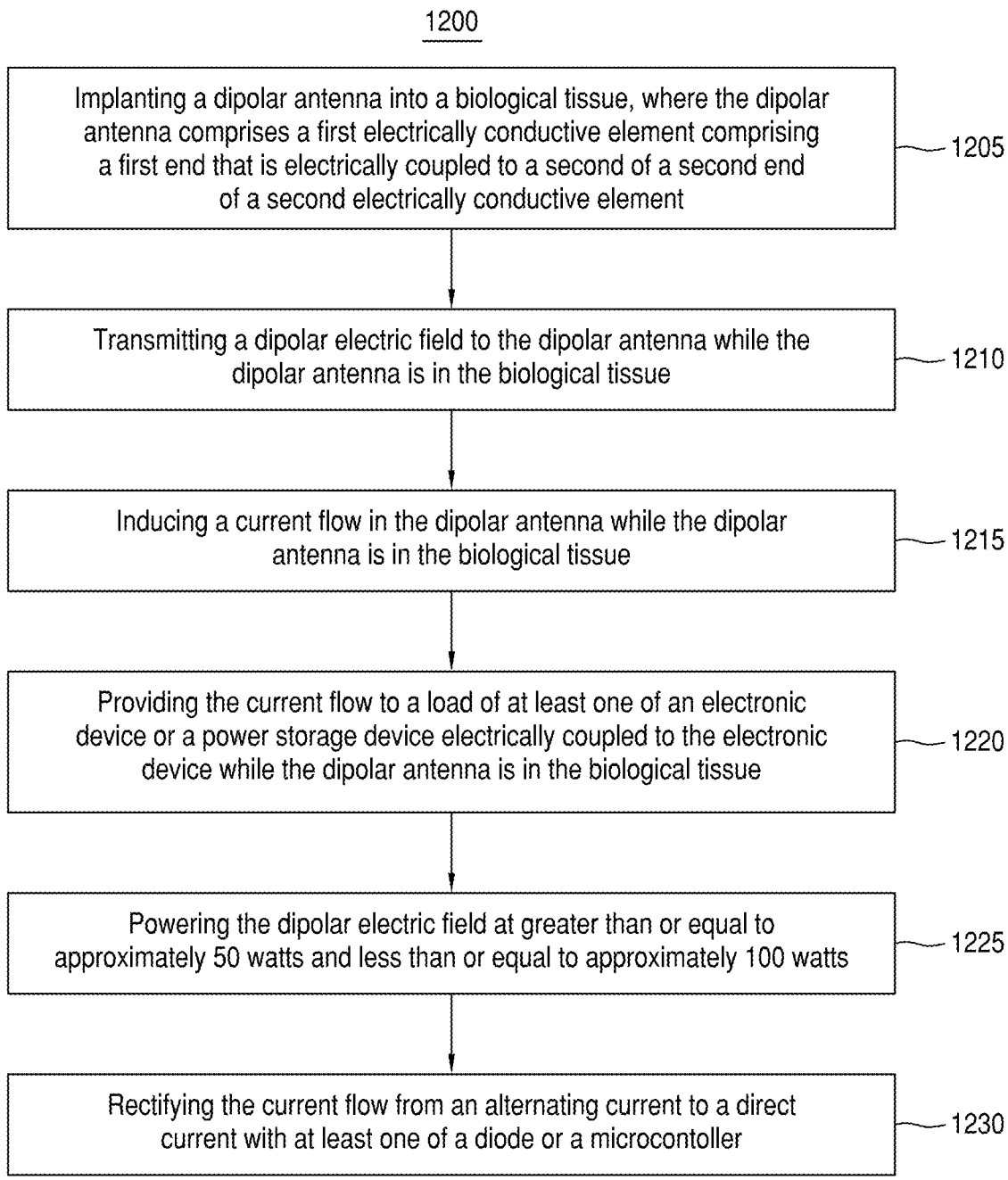
FIG. 12 illustrates a flow chart for an embodiment of another method.

Returning once again to the drawings, FIG. 12 illustrates a flow chart for an embodiment of a method 1200. Method 1200 is merely exemplary and is not limited to the embodiments presented herein. Method 1200 can be employed in many different embodiments or examples not specifically depicted or described herein. In some embodiments, the procedures, the processes, and/or the activities of method 1200 can be performed in the order presented. In other embodiments, the procedures, the processes, and/or the activities of method 1200 can be performed in any other suitable order. In still other embodiments, one or more of the procedures, the processes, and/or the activities of method 1200 can be combined or skipped.

Referring now to FIG. 12, in many embodiments, method 1200 can comprise a procedure 1205 of implanting an electronic device and/or a dipolar antenna into a biological tissue, where the dipolar antenna comprises a first electrically conductive element comprising a first end that is electrically coupled to a second end of a second electrically conductive element. In many embodiments, procedure 1205 of implanting the dipolar antenna into the biological tissue can comprise injecting the dipolar antenna into the biological tissue with a syringe. In the same or different embodiments, the dipolar antenna can be similar to dipolar antenna 910 (FIG. 9), as described above. In the same or different embodiments, the biological tissue can be similar to the biological tissue of apparatus 900 (FIG. 9), as described above. In the same or different embodiments, the syringe can be similar to syringe 980 (FIG. 9), as described above. In the same or different embodiments, the electronic device can be similar to electronic device 901 (FIG. 9), as described above.

Referring back to FIG. 12, in many embodiments, method 1200 can comprise a procedure 1210 of transmitting a dipolar electric field to the dipolar antenna while the dipolar antenna is in the biological tissue. In the same or different embodiments, the dipolar field can be similar to the dipolar field of apparatus 900 (FIG. 9), as described above.

Figure 13:
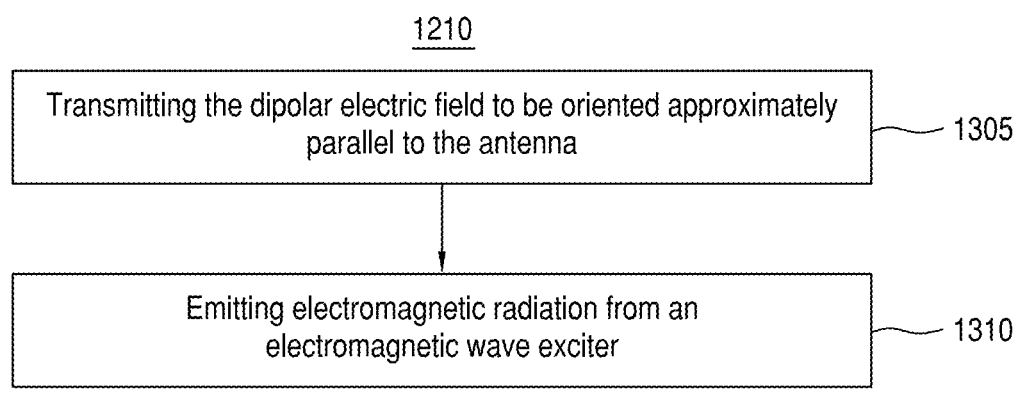
FIG. 13 illustrates a flow chart for an embodiment of a procedure of transmitting the dipolar electric field to the dipolar antenna of the method of FIG. 12.

Referring now to FIG. 13, in many embodiments, procedure 1210 (FIG. 12) of transmitting the dipolar electric field to the dipolar antenna can comprise a process 1305 of transmitting the dipolar electric field to be oriented approximately parallel to the antenna. In other embodiments, procedure 1210 (FIG. 12) of transmitting the dipolar electric field to the dipolar antenna can comprise a process of transmitting the dipolar electric field to be oriented other than approximately parallel to the antenna. The external body antenna can also comprise other configurations. For example, the external body antenna can comprise one or more patch antennas. These patch antenna(s) can be used in therapeutic heating for treatment of cancer within a body.

Referring to FIG. 13, in the same or different embodiments, procedure 1210 (FIG. 12) can comprise a process 1310 of emitting electromagnetic radiation from an electromagnetic wave exciter. In the same or different embodiments, the electromagnetic radiation can be similar to the electromagnetic radiation of apparatus 900 (FIG. 9), as described above. In the same or different embodiments, the electromagnetic wave exciter can be similar to electromagnetic wave exciter 950 (FIG. 9), as described above.

Figure 14:
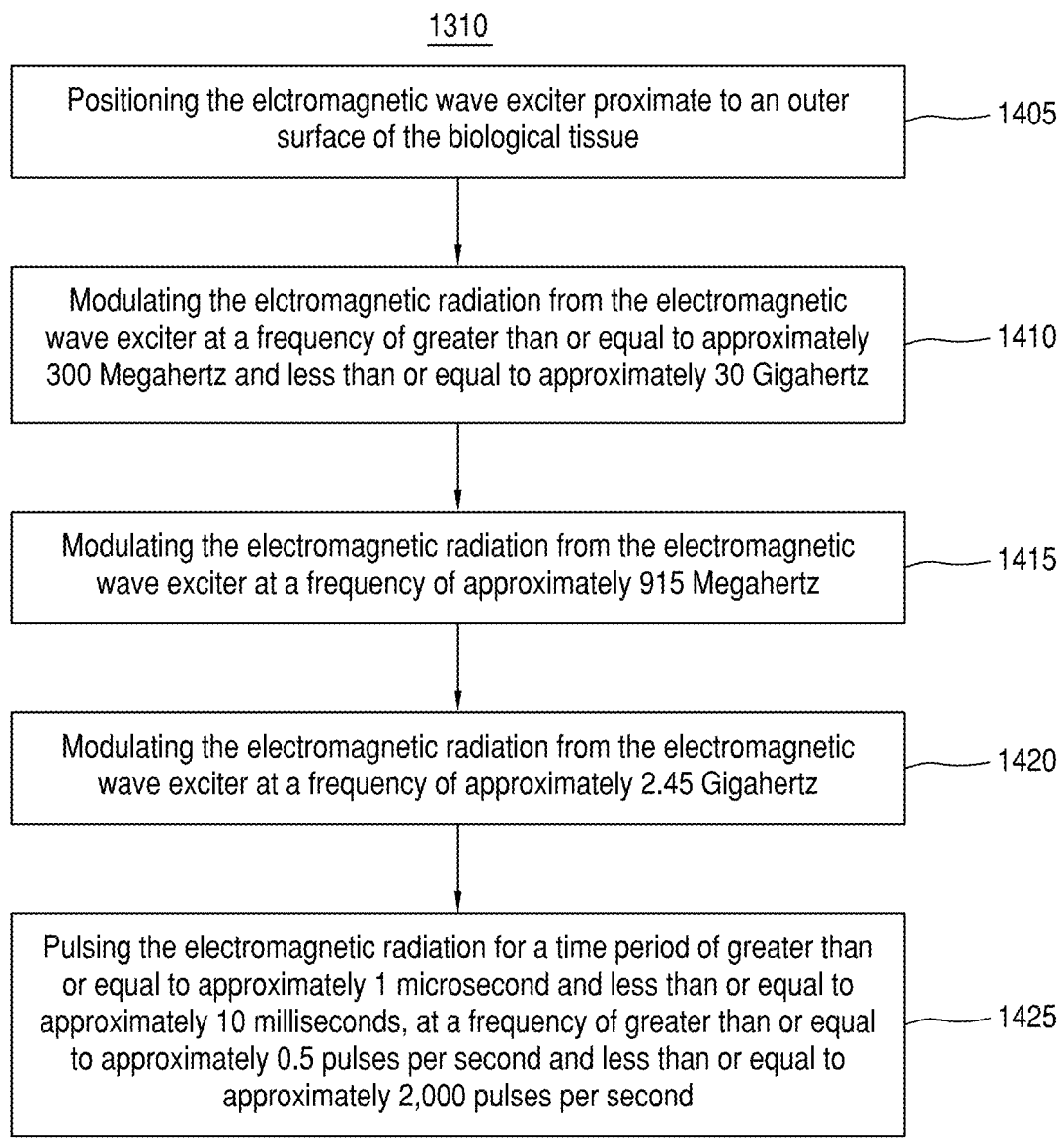
FIG. 14 illustrates a flow chart for an embodiment of a process of emitting electromagnetic radiation from the electromagnetic wave exciter of the procedure of FIG. 13.

Referring now to FIG. 14, in many embodiments, process 1310 (FIG. 13) of emitting electromagnetic radiation from the electromagnetic wave exciter can comprise an activity 1405 of positioning the electromagnetic wave exciter proximate to an outer surface of the biological tissue.

Referring again to FIG. 14, in the same or different embodiments, process 1310 (FIG. 13) can comprise an activity 1410 of modulating the electromagnetic radiation from the electromagnetic wave exciter at a frequency of greater than or equal to approximately 300 Megahertz and less than or equal to approximately 30 Gigahertz. In the same or different embodiments, process 1310 (FIG. 13) can comprise an activity 1415 of modulating the electromagnetic radiation from the electromagnetic wave exciter at a frequency of approximately 915 Megahertz. In the same or different embodiments, process 1310 (FIG. 13) can comprise an activity 1420 of modulating the electromagnetic radiation from the electromagnetic wave exciter at a frequency of approximately 2.45 Gigahertz. In the same or different embodiments, process 1310 (FIG. 13) can comprise an activity 1425 of pulsing and/or bursting the electromagnetic radiation for a time period of greater than or equal to approximately 1 microsecond and less than or equal to approximately 10 milliseconds, at a frequency of greater than or equal to approximately 0.5 pulses per second and less than or equal to approximately 2000 pulses per second.

Referring back to FIG. 12, in many embodiments, method 1200 can comprise a procedure 1215 of inducing a current flow in the dipolar antenna while the dipolar antenna is in the biological tissue. In some embodiments, the current flow can be an alternating current flow.

Referring back to FIG. 12, in many embodiments, method 1200 can comprise a procedure 1220 of providing the current flow to a load of an electronic device and/or a energy storage device electrically coupled to the electronic device while the dipolar antenna and the lead are in the biological tissue. In the same or different embodiments, the electronic device can be similar to electronic device 960 (FIG. 9), as described above. In the same or different embodiments, the energy storage device can be similar to energy storage device 965 (FIG. 9), as described above.

Referring back to FIG. 12, in many embodiments, method 1200 can comprise a procedure 1225 of electrically powering the dipolar electric field at greater than or equal to approximately 50 watts and less than or equal to approximately 100 watts. In other embodiments, method 1200 can comprise a procedure of electrically powering the dipolar electric field at greater than or equal to approximately 10 watts and less than or equal to approximately 300 watts.

Referring back to FIG. 12, in many embodiments, method 1200 can comprise a procedure 1230 of rectifying the current flow from an alternating current to a direct current with a diode and/or a microcontroller. In the same or different embodiments, the diode can be similar to the diode of apparatus 900 (FIG. 9), as described above. In the same or different embodiments, the microcontroller can be similar to the microcontroller of apparatus 900 (FIG. 9), as described above.

Figure 15:
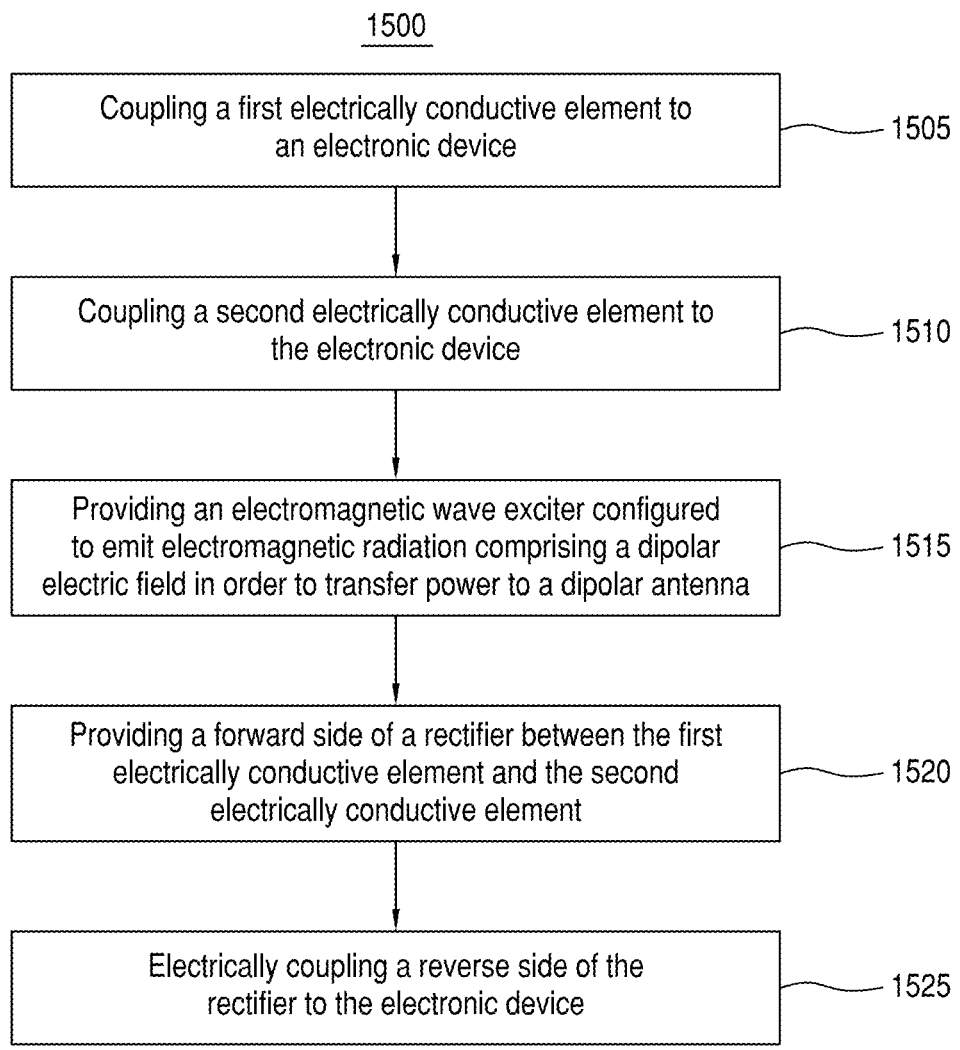
FIG. 15 illustrates a flow chart for an embodiment of another method.

Returning once again to the drawings, FIG. 15 illustrates a flow chart for an embodiment of a method 1500. Method 1500 is merely exemplary and is not limited to the embodiments presented herein. Method 1500 can be employed in many different embodiments or examples not specifically depicted or described herein. In some embodiments, the procedures, the processes, and/or the activities of method 1500 can be performed in the order presented. In other embodiments, the procedures, the processes, and/or the activities of method 1500 can be performed in any other suitable order. In still other embodiments, one or more of the procedures, the processes, and/or the activities of method 1500 can be combined or skipped.

Referring now to FIG. 15, in many embodiments, method 1500 can comprise a procedure 1505 of coupling a first electrically conductive element to an electronic device. Referring again to FIG. 15, in many embodiments, method 1500 can comprise a procedure 1510 of coupling a second electrically conductive element to the electronic device. In the same or different embodiments, the first electrically conductive element can be similar to first electrically conductive element 920 (FIG. 9), as described above. In the same or different embodiments, the second electrically conductive element can be similar to second electrically conductive element 930 (FIG. 9), as described above. In the same or different embodiments, the electronic device can be similar to electronic device 960 (FIG. 9), as described above.

In the same or different embodiments, the first and second electrically conductive elements can form a dipolar antenna. In the same or different embodiments, the dipolar antenna can be similar to dipolar antenna 910 (FIG. 9), as described above. In the same or different embodiments, the electronic device can be similar to electronic device 960 and/or can comprise an energy storage device. In the same or different embodiments, the energy storage device can be similar to energy storage device 965 (FIG. 9), as described above.

Referring now to FIG. 15, in many embodiments, method 1500 can comprise a procedure 1515 of providing an electromagnetic wave exciter configured to emit electromagnetic radiation comprising a dipolar electric field in order to transfer energy to the dipolar antenna. In the same or different embodiments, the electromagnetic wave exciter can be similar to electromagnetic wave exciter 950. In the same or different embodiments, the electromagnetic radiation and/or the dipolar electric field can be similar to the electromagnetic radiation and/or the dipolar electric field of apparatus 900, as described above.

In the same or different embodiments, the electromagnetic wave exciter can be configured to emit the electromagnetic radiation at a frequency greater than or equal to approximately 300 Megahertz and less than or equal to approximately 30 Gigahertz. In the same or different embodiments, the electromagnetic wave exciter can be configured to emit the electromagnetic radiation at a frequency of approximately 915 Megahertz. In the same or different embodiments, the electromagnetic wave exciter can be configured to emit the electromagnetic radiation at a frequency of approximately 2.45 Gigahertz. In the same or different embodiments, the electromagnetic wave exciter can comprise an energy source capable of supplying a peak power level greater than or equal to approximately 10 watts and less than or equal to approximately 100 watts and an average power level greater than or equal to approximately 1 watt and less than or equal to approximately 10 watts. In the same or different embodiments, the electromagnetic wave exciter can be configured to pulse and/or burst the electromagnetic radiation for a time period of greater than or equal to approximately 1 microsecond and less than or equal to approximately 10 milliseconds, at a frequency of greater than or equal to approximately 0.5 pulses per second and less than or equal to approximately 2000 pulses per second.

Referring now to FIG. 15, in many embodiments, method 1500 can comprise a procedure 1520 of providing a forward side of a rectifier between the first electrically conductive element and the second electrically conductive element. In the same or different embodiments, method 1550 can comprise a procedure 1525 of coupling electrically a reverse side of the rectifier to the electronic device. In the same or different embodiments, the rectifier can be similar to rectifier 970 (FIG. 9), as described above.

Referring once again to the drawings, FIGS. 16-19 and the following disclosure corresponding thereto, relate to various embodiments described above with respect to FIGS. 9-15. In many of these embodiments, a high frequency electromagnetic wave, typically in the Gigahertz frequency microwave region can be applied to biological tissue, typically using a body surface placement of a dipole, patch, or any conventional compact microwave antenna. In the same or different embodiments, a second, typically much shorter and smaller dipolar antenna can be implanted into the biological tissue. In some embodiments, the second dipolar antenna can consist of two separate electrical wires insulated along their length and mutually connected at their base ends to an electrical load. In various embodiments, with a parallel orientation between the external antenna and internal antenna, the devices will electrically couple primarily through their electric fields, resulting in an electric field distribution within the wires. In the same or different embodiments, the resulting electric field can induce a current flow in the load connected at the base of the wires. In further embodiments, the load may rectify the high frequency microwave field to present a direct current for electrically powering implanted electronic devices. In many examples, these energy transfer apparatuses and methods can permit microelectronic implants in body tissue to be a form factor that is long and thin, advantageously allowing the electrical devices to be injected using a thin tube such as syringe needle rather than requiring surgical placement within the body. In further examples, such apparatuses and methods can be devoid of inductive coils of large area ordinarily used to couple energy into bioelectronic medical implants.

In the near field of coupling and at frequencies below about 30 MHz often used, the on axis magnetic field declines according to the well-known formula (derived from the Biot-Savart law):

$$B = \frac{\mu_0 I R^2}{2(R^2 + \chi^2)^{3/2}}$$

Where: u=the permeability constant, i=coil current, in amperes, r=coil radius, in meters, x=coil distance, on axis, to point, in meters. Thus along the axis of separation, the field declines rapidly by a cube relationship when x>>r. Due to the need for a two-dimensional loop with an area the implanted coil diameters tend to be comparable in diameter to the depth that they need to be implanted in body tissue.

Although magnetic coupling works reasonably well for devices with coupled coils of dimension in the centimeter range, and for implantation depths of a few centimeters such as pulse generators, pacemakers, and similar devices, it works poorly for coupling into millimeter scale medical devices implanted at many centimeter depths. The problem is that magnetic coupling between two coils having inductance L that are open loop area A dependent $$L=\mu N^2 A/l$$

separated by multiples of their diameter, exhibit very low coupling coefficients, k. Accordingly, a mutual coupling of two coils is dependent largely on their separation and, although its derivation is not given in detail here, is dependent on the coupling coefficient k:

$$k=(L1L2)^{0.5}/M$$

The end result is that it becomes difficult and involves high losses to inductively electrically power very small devices that, for example, will pass through a syringe needle and need to be placed deep into tissues due to their coupling coefficients being exceedingly small, and far less than unity.

Many investigators have previously assumed that high frequency couplings to implanted bioelectronic devices are not efficient or feasible due to the strong absorption of microwave by body tissue. Their coupling is mostly capacitive in the near field and so coupling is partially through a direct proximity capacitance reactance:

$$C=e_rA/d$$

as well as some fraction of direct electromagnetic wave propagation if the implantation depth is multiple wavelengths in body tissue.

Although microwave attenuation losses in the range of 300 Megahertz-30 Gigahertz are much greater than those losses of frequencies in the tens of Megahertz, changes in body tissue impedance with frequency and the increase in coupling between wire antennas through the electric field component can offset this loss. The effects of electric field displacement currents that can become important in these higher ranges. In many examples, the higher frequencies can allow for greater efficiency in detection with small wire antennas which is a consideration in making small bioelectronic medical implants.

In many examples, the length of the implant antenna can be shortened relative to a microwave dipole in air in the low GHz frequency region. In some examples, this shortening can occur because the wavelength of electromagnetic energy is shorter due to the elevated tissue dielectric constant (about 50-80) which shortens the wavelength relative to free space. This shortening can be fortuitous since it effects an overall reduction in the size of the implant dipole length by the square root of the dielectric constant. Thus half wave antennas of approximately a centimeter or so in length for implants can be feasible at GHz frequencies, and their short length can lend to practical implant lengths for minimally invasive placement through syringe needles.

In many examples, energy coupling between aligned dipolar antennas in the microwave frequency range of 300 MHz to 30 GHz can be achieved between implanted devices and external antennas with useful efficiency. Energy losses, although not insignificant, are tolerable for implant depths of more than ten centimeters in the transference with losses on the order of 2-3 db/cm at 915 MHz depending on tissue types. In many examples, fat and bone are far less attenuative than muscle or blood. Energy transfer by microwave to deep lying implants >10 cm can clearly suffer large attenuations; however, modern microelectronic implants are typically designed for low power, often in the milliwatt to microwatt ranges, so average power energy transfers in this range can be achieved using power levels to the skin on the order of one watt, as is typical of the power level of a cell phone and within the specific absorption rate (SAR) limits of safety. In the same or different examples, losses of 30 db over a path length of 10 cm to an implanted device can be acceptable to supporting its momentary function. In some examples, it may not be sufficient to charge its internal batteries except if the device is closer to the body surface.

In various embodiments, where rectification of the energy occurs, higher pulsed power levels, on the order of tens of watts, at proportionally lower duty cycles to achieve the same safe average power can be used to transfer pulses of higher amplitude that are useful to overcome thresholds of Schottky diode types of rectifiers.

In further examples, needle-like antennas on the order of less than a millimeter in diameter and up to several centimeters in length can be achieved, used, and introduced into the human body through the lumen of needles, as opposed to surgical implantation of loops, and so can avoid surgery.

In many embodiments, a high frequency electromagnetic generator in the range of 300 MHz to 30 GHz can be electrically coupled to a dipolar antenna placed on or near the surface of tissue. One embodiment can use 915 MHz or 2.45 GHz or another microwave frequency so as to be consistent with commonly used communication bands allocated for this purpose.

Some embodiments can comprise an antenna comprising a simple wire dipole antenna with each arm of the dipole approximately 7 cm in length so as to tune the antenna for resonance when placed near or in contact with biological tissue. In further embodiments, a patch antenna or other conventional antenna presenting a strong electric field component in tissue can be used. Other embodiments can comprise an antenna consisting of a simple wire dipole antenna with each arm of the dipole approximately 7 cm in length so as to tune the antenna for resonance when placed near or in contact with biological tissue.

In various embodiments, an implanted dipole antenna can comprise two end-to-end conductors insulated along their length and mutually connected to an electrical load at their base ends such that an electrical field is induced across the load at the exciter frequency. In some embodiments, for certain configurations where the half wavelength is near the implant length, the conductor wire tips can be left uninsulated and touching biological tissue. Thus this forms a dipole antenna that it is long and thin and therefore suited for implantation in body tissue through a small tube. The length of this antenna for body implantation in biological tissue, for example, can be less than 1 cm for ease of introduction but may be 5 cm or more for increased performance at ~15 cm depths in biological tissue. In many embodiments, the load of the system can comprise a rectifier of the high frequency electric field such that the rectifier produces a half or full wave rectification with subsequent application of the energy to electrically power activities within the implant. In some embodiments, electrical energy can be tapped off the rectifier by an isolating choke and leads attached locally to the rectifier contacts so as to present minimal interference with the ability of the system to couple to the microwave field.

In operation, short intense pulses or steady application of the external electromagnetic field resulting in acceptable levels of total energy applied to body tissues are applied by the exciter to the skin surface and so induce currents in the implanted device load. The rectified output of this system may be used to charge an internal capacitor, battery, or may be directly used to electrically power a digital or other system for actuation, sensing, or telemetry.

Figure 16:
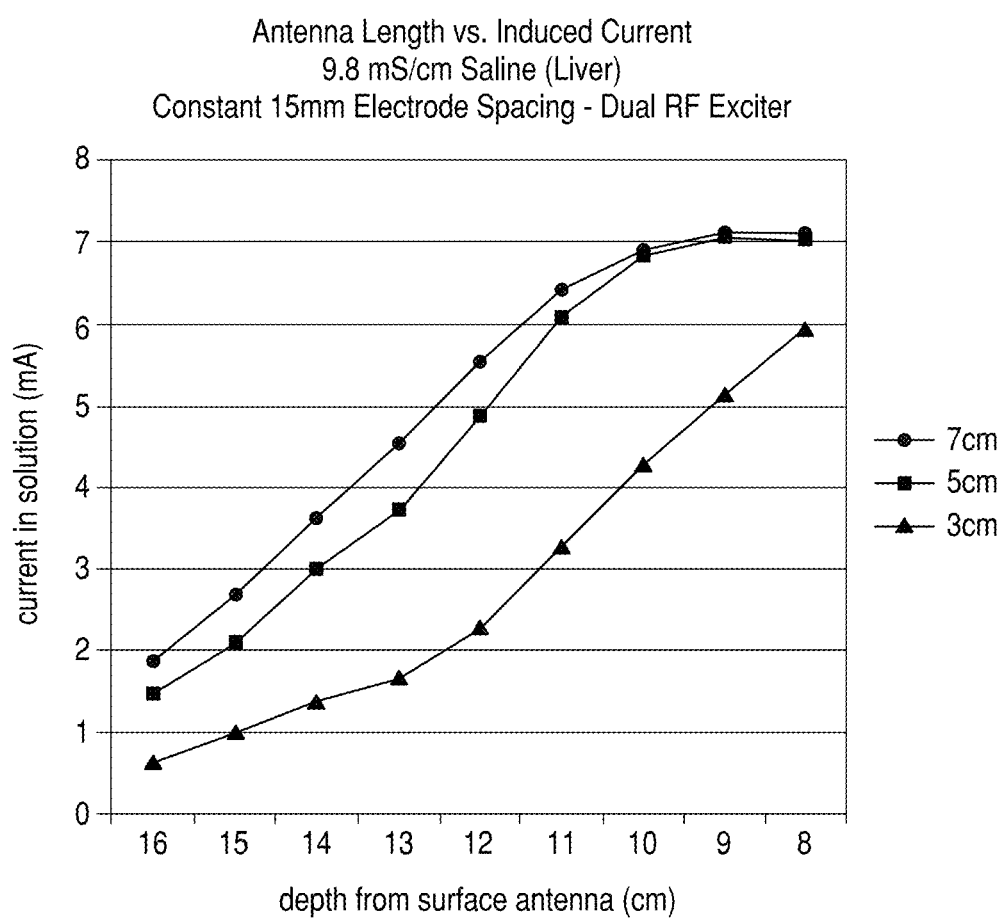
FIG. 16 is a graph plotting an exemplary current flow induced in a load resistor after rectification as a function of the tissue depth.
Figure 17:
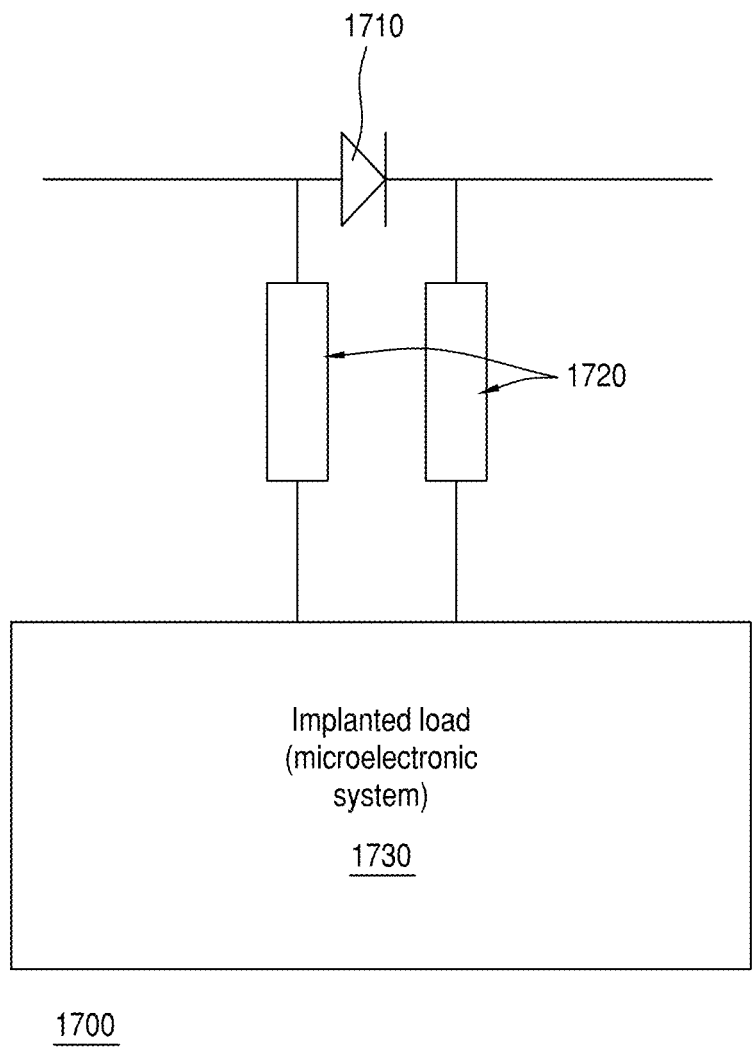
FIG. 17 illustrates an exemplary schematic of an implanted energy harvesting system employing an optional rectifier and an isolating choke at the load.

Referring now back to the drawings, FIG. 16 provides exemplary experimental data derived from using a salt water tank model to stimulate biological tissue. FIG. 16 illustrates the current flow induced in a load resistor after rectification (y-axis) as a function of the tissue depth (x-axis). The applied exciter emitted 300 watt pulses of microwave energy at 915 Megahertz into a salt solution to simulate the conductivity of the tissue of a human liver. The electrical energy inducted into the submerged antenna was rectified by a CDF7431 Skyworks Schottky diode and presented a value of current generated in a volume conductor load. FIG. 17 illustrates an exemplary schematic of an implanted energy harvesting system 1700 employing an optional rectifier 1710 and an isolating choke 1720 at load 1730.

Figure 18:
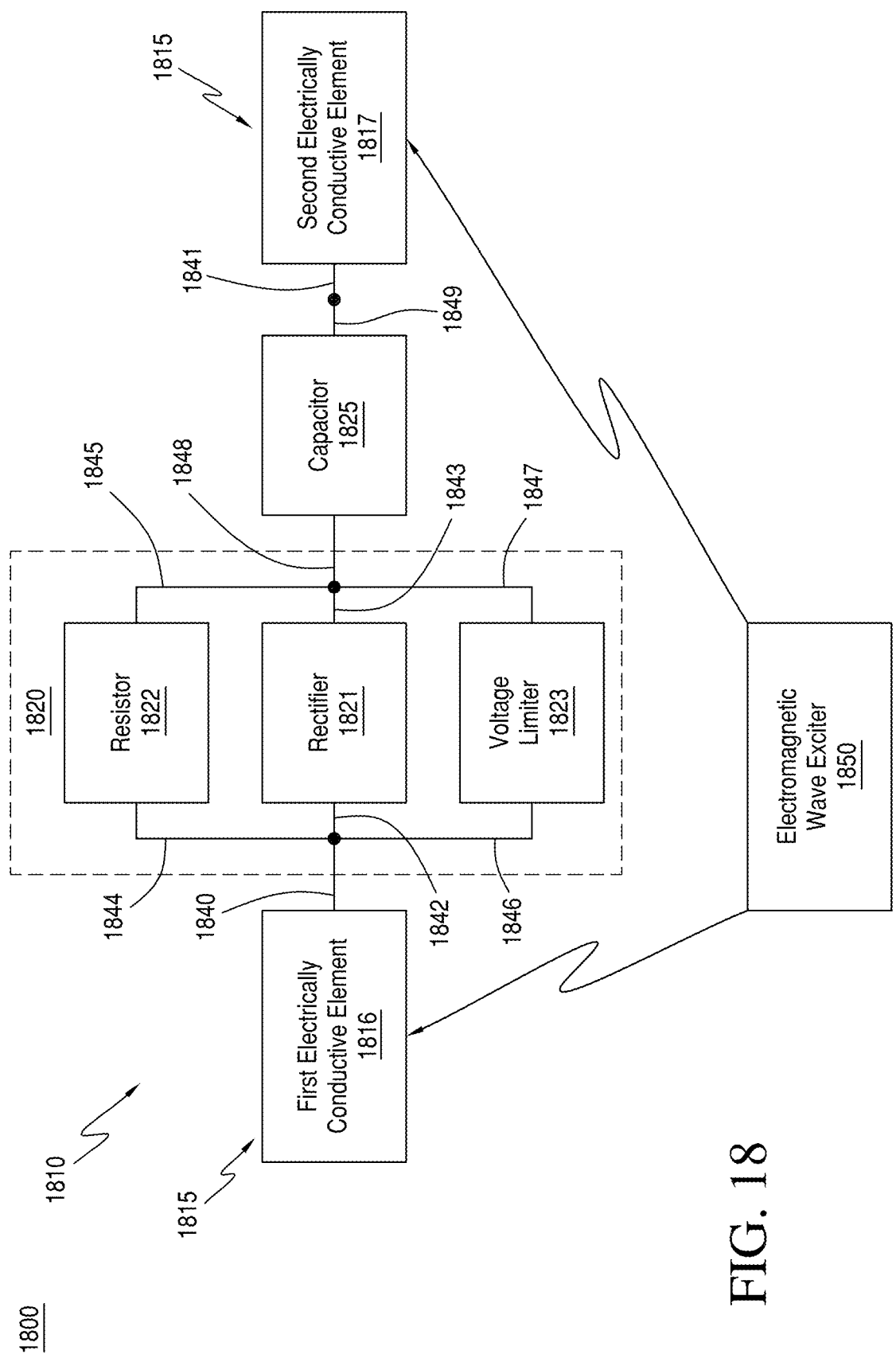
FIG. 18 is a schematic block diagram illustrating an embodiment of another system.

Referring now back to the drawings, FIG. 18 illustrates a system 1800, according to an embodiment of system 1800. System 1800 is merely exemplary and is not limited to the embodiments presented herein. System 1800 can be employed in many different embodiments or examples not specifically depicted or described herein.

Referring now to FIG. 18, system 1800 comprises apparatus 1810. Apparatus 1810 comprises dipolar antenna 1815. In many embodiments, dipolar antenna 1815 comprises first electrically conductive element 1816 and second electrically conductive element 1817. In some embodiments, first electrically conductive element 1816 and/or second electrically conductive element 1817 can be similar to first electrically conductive element 920 (FIG. 9) and/or second electrically conductive element 930 (FIG. 9), respectively, as described above. In the same or different embodiments, dipolar antenna 1815 can be configured to receive a dipolar electric field. In some embodiments, the dipolar electric field can be similar to the dipolar electric field described above with respect to apparatus 900 (FIG. 9). In other embodiments, dipolar antenna 1815 can be similar to dipolar antenna 910 (FIG. 9).

In some embodiments, apparatus 1810 can be configured to be implanted in biological tissue. In the same or different embodiments, the biological tissue can be similar to the biological tissue described above with respect to apparatus 900 (FIG. 9). For example, in some embodiments, apparatus 1810 can be implanted in a human torso, and electromagnetic wave exciter 1850, as described in further detail below, can be placed at the human chest and/or back. In many embodiments, first electrically conductive element 1816 and second electrically conductive element 1817 can each be configured to be electrically coupled with the biological tissue.

In some embodiments, apparatus 1810 can be configured to pass through a lumen of a 14 gauge needle, a 15 gauge needle, a 16 gauge needle, a 17 gauge needle, an 18 gauge needle, a 19 gauge needle, a 20 gauge needle, a 21 gauge needle, and/or a 22 gauge needle of a syringe. In the same or different embodiments, the syringe can be similar to syringe 980 (FIG. 9). In some embodiments, system 1800 can comprise the syringe, wherein apparatus 1810 is located within the syringe. In other embodiments, system 1800 and/or apparatus 1810 can be separate from the syringe.

Referring again to FIG. 18, apparatus 1810 comprises sub-circuit 1820. Sub-circuit 1820 comprises rectifier 1821, resistor 1822, and voltage limiter 1823. In the same or different embodiments, rectifier 1821, resistor 1822, and voltage limiter 1823 are electrically coupled in parallel with each other. In many embodiments, rectifier 1821 can comprise one or more diodes. In the same or different embodiments, the one or more diodes can comprise one or more Schottky diodes. In some embodiments, rectifier 1821 can be similar to rectifier 970 (FIG. 9), as described above. In the same or different embodiments, voltage limiter 1823 can comprise a Zener diode and/or at least two radio frequency diodes electrically coupled in series with each other. In various embodiments, resistor 1822 can comprise an electrical resistance greater than or equal to approximately 500 ohms and less than or equal to approximately 10,000 ohms.

Referring again to FIG. 18, apparatus 1810 comprises capacitor 1825. In various embodiments, capacitor 1825 can comprise an electrical capacitance of greater than or equal to approximately 0.1 microfarads and less than or equal to 10 microfarads.

Referring again to FIG. 18, in many embodiments, first electrically conductive element 1816, sub-circuit 1820, capacitor 1825, and second electrically conductive element 1817 are electrically coupled in series with each other. In the same or different embodiments, first electrically conductive element 1816 can comprise first element connector 1840. Second electrically conductive element 1817 can comprise second element connector 1841. Rectifier 1821 can comprise first rectifier connector 1842 and second rectifier connector 1843. Resistor 1822 can comprise first resistor connector 1844 and second resistor connector 1845. Voltage limiter 1823 can comprise first voltage limiter connector 1846 and second voltage limiter connector 1847. Capacitor 1825 can comprise first capacitor connector 1848 and second capacitor connector 1849. In many embodiments, first rectifier connector 1842, first resistor connector 1844, and first voltage limiter connector 1846 are electrically coupled to first element connector 1840. In the same or different embodiments, second rectifier connector 1843, second resistor connector 1845, and second voltage limiter connector 1847 are electrically coupled to first capacitor connector 1848. In the same or different embodiments, second capacitor connector 1849 is electrically coupled to second element connector 1841.

Referring again to FIG. 18, system 1800 can comprise electromagnetic wave exciter 1850 configured to emit electromagnetic radiation comprising the dipolar electric field. In the same or different embodiments, system 1800 can be configured to transfer electric power between electromagnetic wave exciter 1830 and dipolar antenna 1815 and/or apparatus 1810 through the dipolar electric field of the electromagnetic radiation. In various embodiments, electromagnetic wave exciter 1850 can be similar to electromagnetic wave exciter 950 (FIG. 9). In some embodiments, the electromagnetic radiation can be similar to the electromagnetic radiation described above with respect to apparatus 900 (FIG. 9).

In some embodiments, apparatus 1810 can be configured to provide pulses of electric current to the biological tissue when: (a) electromagnetic wave exciter 1850 emits electromagnetic radiation such that dipolar antenna 1815 receives the dipolar electric field of the electromagnetic radiation; and (b) first electrically conductive element 1816 and second electrically conductive element 1817 are electrically coupled to the biological tissue. In the same or different embodiments, apparatus 1810 can be configured to stimulate the biological tissue by providing the pulses of electric current to the biological tissue. In some embodiments, the pulses of electric current can comprise pulse durations greater than or equal to approximately 60 microseconds and less than or equal to approximately 250 microseconds. In the same or different embodiments, the pulses of electric current can comprise pulse repetition rates greater than or equal to approximately 100 Hertz.

For example, in many embodiments, when dipolar antenna 1815 receives the dipolar electric field of the electromagnetic radiation emitted from electromagnetic wave exciter 1850, the dipolar electric field induces a flow of electric current in dipolar antenna 1815 such that the flow of electric current passes from first electrically conductive element 1816 to and through rectifier 1821. Capacitor 1825 can block the steady direct electric current passing through rectifier 1821 and pulse the electric current as it flows through capacitor 1825 to second electrically conductive element 1817 to complete the circuit formed by apparatus 1810. In the same or different embodiments, because rectifier 1821 permits only unidirectional flow of electric current, resistor 1822 can provide a shunt across rectifier 1821 to permit the electric current passing from second electrically conductive element 1817 back through capacitor 1825 to flow back to first electrically conductive element 1816. Accordingly, the electric current flowing back through resistor 1822 and any electric current leaking back through rectifier 1821 can then permit capacitor 1825 to recharge in order to provide another pulse of the electric current to the biological tissue. The resulting pulses of electric current delivered to the biological tissue thereby electrically stimulates the biological tissue in which apparatus 1810 is implanted.

Resistor 1822 can also discharge a polarization of first electrically conductive element 1816 and second electrically conductive element 1817. The resistance rating of resistor 1822 can be sufficiently higher than the threshold voltage of rectifier 1821 so that the electric current will flow forward through rectifier 1821 rather than attempting to bypass rectifier 1821 by flowing forward through resistor 1821; however, because lower resistance ratings for resistor 1822 can provide faster recovery times of the applied electric current pulse, it may be desirable to use the resistance rating of resistor 1822 that optimally balances these two concerns. Meanwhile, increasing the electric capacitance of capacitor 1825 can provide for higher repetition rates (e.g., in the 1 millisecond range) at the tradeoff of decreased rectification efficiency of rectifier 1821. Accordingly, it may also be desirable to find a capacitance rating that balances these concerns. The resistance and/or capacitance ratings provided above for resistor 1822 and/or capacitor 1825, respectively, comprise possible resistance and/or capacitance ratings for resistor 1822 and/or capacitor 1825.

In the same or different embodiments, for purposes of safety, rectifier 1821 can be further shunted by voltage limiting circuit 1823. As an example, voltage limiting circuit 1823 can prevent an overvoltage of approximately 1-10 volts or higher.

Returning once again to the drawings, FIG. 19 illustrates a flow chart for an embodiment of a method 1900 of providing a system. In some embodiments, the system can be similar to system 1800, as described above. Method 1900 is merely exemplary and is not limited to the embodiments presented herein. Method 1900 can be employed in many different embodiments or examples not specifically depicted or described herein. In some embodiments, the procedures, the processes, and/or the activities of method 1900 can be performed in the order presented. In other embodiments, the procedures, the processes, and/or the activities of method 1900 can be performed in any other suitable order. In still other embodiments, one or more of the procedures, the processes, and/or the activities of method 1900 can be combined or skipped.

Referring now to FIG. 19, method 1900 comprises procedure 1905 of providing a dipolar antenna configured to receive a dipolar electric field, the dipolar antenna comprising a first conductive element and a second conductive element. In some embodiments, the dipolar antenna can be similar to dipolar antenna 1815 (FIG. 18), as described above. In the same or different embodiments, the dipolar electric field can be similar to the dielectric field described above with respect to apparatus 900 (FIG. 9). In the same or different embodiments, the first conductive element and/or the second conductive element can be similar to first conductive element 1816 (FIG. 18) and/or second conductive element 1817 (FIG. 18), respectively. Procedures 1905, 1910, 1915, 1920, and 1925 can be performed in any sequence.

Afterwards, referring again to FIG. 19, method 1900 comprises procedure 1910 of providing a rectifier. Method 1900 comprises procedure 1915 of providing a resistor. Method 1900 comprises procedure 1920 of providing a voltage limiter. Method 1900 comprises procedure 1925 of providing a capacitor. In the same or different embodiments, the rectifier, the resistor, the voltage limiter, and/or capacitor can be similar to rectifier 1821, resistor 1822, voltage limiter 1823, and/or capacitor 1825 (FIG. 18), respectively, as described above.

Referring again to FIG. 19, method 1900 comprises procedure 1930 of coupling the rectifier electrically in parallel with the resistor and the voltage limiter to form a sub-circuit. In the same or different embodiments, the sub-circuit can be similar to sub-circuit 1820 (FIG. 18).

Referring again to FIG. 19, method 1900 comprises procedure 1935 of coupling the sub-circuit electrically in series with the first conductive element, the capacitor, and the second conductive element to form an apparatus configured to be implanted in biological tissue. In the same or different embodiments, the apparatus can be similar to apparatus 1810 (FIG. 18). In the same or different embodiments, the biological tissue can be similar to the biological tissue described above with respect to apparatus 900 (FIG. 9).

Referring again to FIG. 19, procedures 1930 and 1935 can be restated as procedures 1940, 1945, and 1950. For example, method 1900 can comprise procedure 1940 of coupling electrically a first rectifier connector of the rectifier, a first resistor connector of the resistor, and a first voltage limiter connector of the voltage limiter with a first element connector of the first electrically conductive element. Method 1900 also can comprise procedure 1945 of coupling electrically a second rectifier connector of the rectifier, a second resistor connector of the resistor, and a second voltage limiter connector of the voltage limiter with a first capacitor connector of the capacitor. Method 1900 can further comprise procedure 1950 of coupling electrically a second capacitor connector of the capacitor with a second element connector of the second electrically conductive element.

Referring again to FIG. 19, after procedure 1935 or 1950, method 1900 can comprise procedure 1955 of providing an electromagnetic wave exciter configured to emit electromagnetic radiation comprising the dipolar electric field. In the same or different embodiments, the electromagnetic wave exciter can be similar to electromagnetic wave exciter 1850 (FIG. 18). In the same or different embodiments, the electromagnetic radiation and/or the dipolar electric field can be similar to the electromagnetic radiation and/or dipolar electric field described above with respect to apparatus 900 (FIG. 9).

Referring again to FIG. 19, method 1900 can comprise procedure 1960 of coupling electrically the first electrically conductive element and the second electrically conductive element with the biological tissue.

Figure 20:
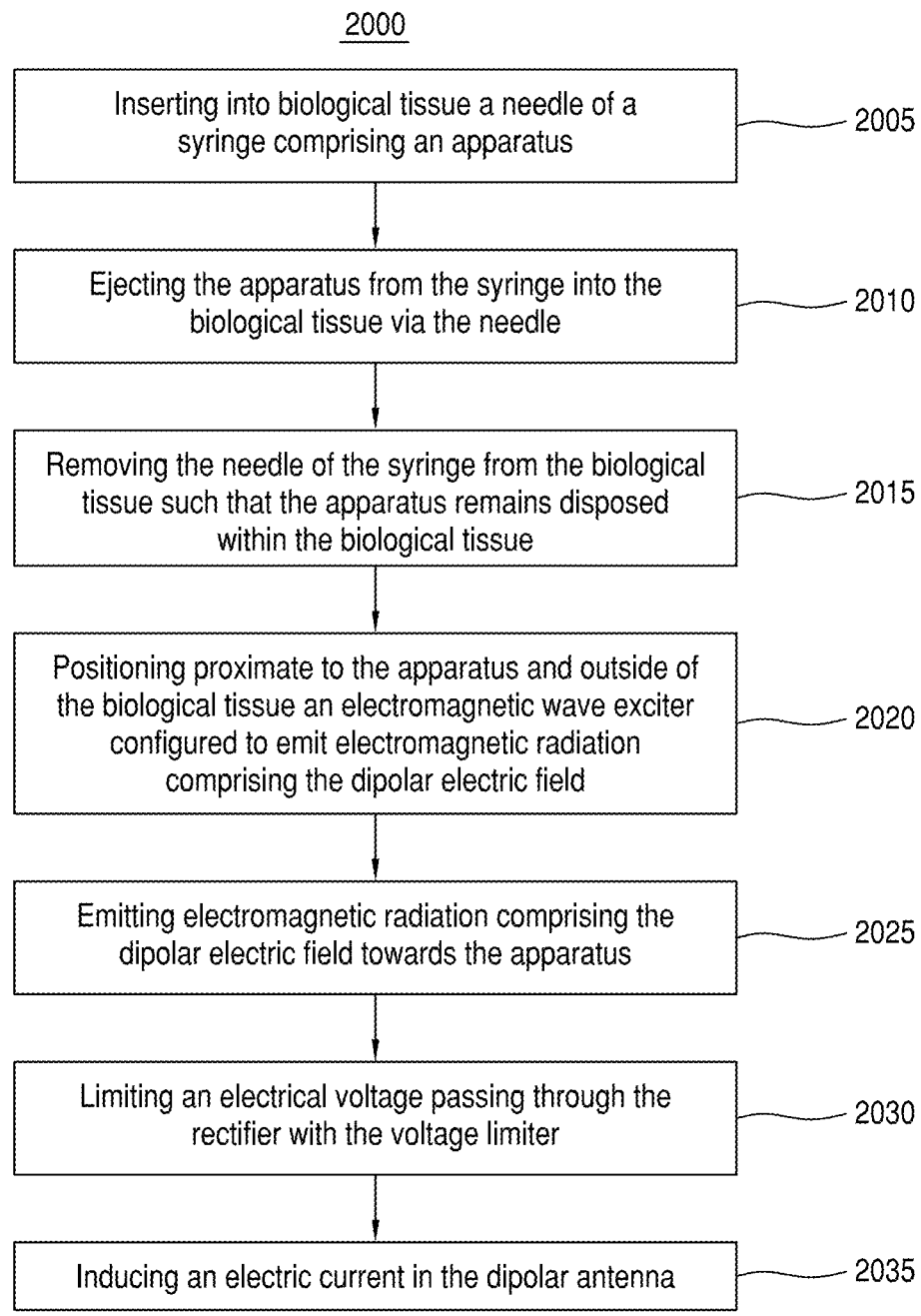
FIG. 20 illustrates a flow chart for an embodiment of yet another method.

Returning once again to the drawings, FIG. 20 illustrates a flow chart for an embodiment of a method 2000. Method 2000 is merely exemplary and is not limited to the embodiments presented herein. Method 2000 can be employed in many different embodiments or examples not specifically depicted or described herein. In some embodiments, the procedures, the processes, and/or the activities of method 2000 can be performed in the order presented. In other embodiments, the procedures, the processes, and/or the activities of method 2000 can be performed in any other suitable order. In still other embodiments, one or more of the procedures, the processes, and/or the activities of method 2000 can be combined or skipped.

Referring now to FIG. 20, method 2000 comprises procedure 2005 of inserting into biological tissue a needle of a syringe comprising an apparatus. In the same or different embodiments, the apparatus can be similar to apparatus 1810 (FIG. 18), as described above. In the same or different embodiments, the biological tissue can be similar to the biological tissue described above with respect to apparatus 900 (FIG. 9). In the same or different embodiments, the syringe can be similar to syringe 980 (FIG. 9), as described above. In the same or different embodiments, procedure 2005 can further comprise inserting a needle of a syringe into the biological tissue to a depth within a few centimeters of a surface of the biological tissue. In other embodiments, procedure 2005 can further comprise inserting a needle of a syringe into the biological tissue to a depth of approximately 10-15 centimeters of the surface of the biological tissue. In many embodiments, procedure 2005 can further comprise aligning the needle of the syringe such that the apparatus is oriented approximately parallel to a surface of the biological tissue. In the same or different embodiments, procedure 2005 can further comprise aligning the needle of the syringe such that the apparatus is oriented other than approximately parallel to a surface of the biological tissue. In the same or different embodiments, procedure 2005 can further comprise injecting the needle into the biological tissue.

Referring again to FIG. 20, method 2000 comprises procedure 2010 of ejecting the apparatus from the syringe into the biological tissue via the needle. Referring again to FIG. 20, method 2000 comprises procedure 2015 of removing the needle of the syringe from the biological tissue such that the apparatus remains disposed within the biological tissue.

Referring again to FIG. 20, method 2000 can comprise procedure 2020 of positioning proximate to the apparatus and outside of the biological tissue an electromagnetic wave exciter configured to emit electromagnetic radiation comprising the dipolar electric field. In the same or different embodiments, procedure 2020 can occur after procedures 2005, 2010, and 2015 occur. In the same or different embodiments, the electromagnetic wave exciter can be similar to electromagnetic wave exciter 1850 (FIG. 18). In the same or different embodiments, the electromagnetic radiation and/or the dipolar electric field can be similar to the electromagnetic radiation and/or the dipolar electric field described above with respect to apparatus 900 (FIG. 9). In the same or different embodiments, procedure 2020 can further comprise positioning within approximately 2-4 centimeters of the apparatus the electromagnetic wave exciter configured to emit electromagnetic radiation comprising the dipolar electric field. In the same or different embodiments, procedure 2020 can further comprise positioning within approximately 10-15 centimeters of the apparatus the electromagnetic wave exciter configured to emit electromagnetic radiation comprising the dipolar electric field.

Referring again to FIG. 20, method 2000 can comprise procedure 2025 of emitting electromagnetic radiation comprising the dipolar electric field towards the apparatus. In the same or different embodiments, procedure 2025 can occur after procedures 2005, 2010, and 2015 occur. In some embodiments, procedure 2025 can further comprise modulating the electromagnetic radiation at a frequency of greater than or equal to approximately 300 Megahertz and less than or equal to approximately 30 Gigahertz.

Referring again to FIG. 20, method 2000 can comprise procedure 2030 of limiting an electrical voltage passing through the rectifier with the voltage limiter. In the same or different embodiments, procedure 2030 can occur after procedures 2005, 2010, and 2015 occur. In the same or different embodiments, the voltage limiter can be similar to voltage limiter 1823.

Referring again to FIG. 20, method 2000 can comprise procedure 2035 of inducing an electric current in the dipolar antenna. In the same or different embodiments, procedure 2035 can occur after procedures 2005, 2010, 2015, 2020, 2025, and 2030 occur. In some embodiments, procedure 2035 can further comprise delivering pulses of the electric current to the biological tissue.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that activities 301-306 of FIG. 1, activities 701-707 of FIG. 7, procedures 1005, 1010, and 1015 of FIG. 10, processes 1105 and 1110 of FIG. 11, procedures 1205, 1210, 1215, 1220, 1225, and 1230 of FIG. 12, processes 1305 and 1310 of FIG. 13, activities 1405, 1410, 1415, 1420, 1425, and 1430 of FIG. 14, procedures 1505, 1510, 1515, 1520, and 1525 of FIG. 15, procedures 1905, 1910, 1915, 1920, 1925, 1930, 1935, 1940, 1945, 1950, 1955, and 1960 of FIG. 19, and procedure 2005, 2010, 2015, 2020, 2025, 2030, and 2035 of FIG. 20 may be comprised of many different activities, procedures and be performed by many different modules, in many different orders, that any element of FIGS. 1-20 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

I claim:

1. A method of implanting a first electronic device into biological tissue, the method comprising:
    inserting a needle of a syringe into the biological tissue, wherein:
        the syringe contains the first electronic device;
        the first electronic device comprises:
            a dipolar antenna comprising:
                a first electrically conductive element having a first end; and
                a second electrically conductive element having a second end; and
            a second electronic device;
        the first end and the second end are electrically coupled to the second electronic device;
        the dipolar antenna is configured to provide a current to the second electronic device; and
        the dipolar antenna is configured to receive an electric field with a peak power level greater than or equal to approximately 10 watts and less than or equal to approximately 100 watts and an average power level greater than or equal to approximately 1 watt and less than or equal to approximately 10 watts;
    ejecting the first electronic device from the syringe into the biological tissue; and
    removing the needle of the syringe from the biological tissue such that the first electronic device remains disposed within the biological tissue.

2. The method of claim 1, wherein:
    inserting the needle of the syringe into the biological tissue comprises:
        aligning the needle of the syringe such that the first electronic device is oriented approximately parallel to a surface of the biological tissue; and
        injecting the needle into the biological tissue.

3. The method of claim 1, wherein a combined length of the first electrically conductive element and the second electrically conductive element is greater than or equal to approximately 2 millimeters and less than or equal to approximately 6 centimeters.

4. The method of claim 1, wherein:
    the first electrically conductive element and the second electrically conductive element comprise a biocompatible material; and
    the biocompatible material comprises at least one of platinum, tungsten, palladium, gold, or a biocompatible polymer.

5. The method of claim 1, wherein the needle of the syringe comprises at least one of:
    a 14 gauge needle, a 15 gauge needle, a 16 gauge needle, a 17 gauge needle, an 18 gauge needle, a 19 gauge needle, a 20 gauge needle, a 21 gauge needle, or a 22 gauge needle.

6. The method of claim 1, wherein the second electronic device comprises at least one of:
    a bioelectronic medical sensor, a transducer, a communication system, an actuator, or an energy storage device.

7. The method of claim 1, wherein the dipolar antenna is devoid of an inductive coil.

8. The method of claim 1, wherein:
    at least one of (1) the first electrically conductive element or (2) the second electrically conductive element comprise an insulating outer layer; and
    the insulating outer layer comprises a biocompatible polymer.

9. The method of claim 1, wherein the electric field comprises a dipolar electric field emitted from an electromagnetic wave exciter.

10. An electronic device for implantation into biological tissue via a syringe, the electronic device comprising:
    a dipolar antenna comprising:
        a first electrically conductive element having a first end; and
        a second electrically conductive element having a second end; and
    a second electronic device, wherein:
        the first end and the second end are electrically coupled to the second electronic device;
        the dipolar antenna is configured to provide a current to the second electronic device; and
        the dipolar antenna is configured to receive an electric field with a peak power level greater than or equal to approximately 10 watts and less than or equal to approximately 100 watts and an average power level greater than or equal to approximately 1 watt and less than or equal to approximately 10 watts.

11. The electronic device of claim 10, wherein the electronic device is configured to be inserted into a syringe.

12. The electronic device of claim 11, wherein a needle of the syringe comprises at least one of:
    a 14 gauge needle, a 15 gauge needle, a 16 gauge needle, a 17 gauge needle, an 18 gauge needle, a 19 gauge needle, a 20 gauge needle, a 21 gauge needle, or a 22 gauge needle.

13. The electronic device of claim 10, wherein a combined length of the first electrically conductive element and the second electrically conductive element is greater than or equal to approximately 2 millimeters and less than or equal to approximately 6 centimeters.

14. The electronic device of claim 10, wherein:
    the first electrically conductive element and the second electrically conductive element comprise a biocompatible material; and
    the biocompatible material comprises at least one of platinum, tungsten, palladium, gold, or a biocompatible polymer.

15. The electronic device of claim 10, wherein the second electronic device comprises at least one of:
    a bioelectronic medical sensor, a transducer, a communication system, an actuator, or an energy storage device.

16. The electronic device of claim 10, wherein the dipolar antenna is devoid of an inductive coil.

17. The electronic device of claim 10, wherein:
    at least one of (1) the first electrically conductive element or (2) the second electrically conductive element comprise an insulating outer layer; and
    the insulating outer layer comprises a biocompatible polymer.

18. The electronic device of claim 10, wherein the electric field comprises a dipolar electric field emitted from an electromagnetic wave exciter.

* * * * *